US012561823B2

(12) United States Patent (10) Patent No.: US 12,561,823 B2
Fukuda et al. (45) Date of Patent: Feb. 24, 2026

(54) STRUCTURE ESTIMATION SYSTEM AND STRUCTURE ESTIMATION PROGRAM FOR ESTIMATING HEIGHT OF STRUCTURE BASED ON DATA FROM CHARGED PARTICLE BEAM DEVICE

(71) Applicant: Hitachi High-Tech Corporation, Tokyo (JP)

(72) Inventors: Muneyuki Fukuda, Tokyo (JP); Yasutaka Toyoda, Tokyo (JP); Ryou Yumiba, Tokyo (JP); Shuyang Dou, Tokyo (JP); Ayumi Doi, Tokyo (JP); Junichi Tanaka, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 470 days.

(21) Appl. No.: 17/296,421

(22) PCT Filed: Feb. 15, 2019

(86) PCT No.: PCT/JP2019/005648
§ 371 (c)(1),
(2) Date: May 24, 2021

(87) PCT Pub. No.: WO2020/166076
PCT Pub. Date: Aug. 20, 2020

(65) Prior Publication Data
US 2022/0130027 A1 Apr. 28, 2022

(51) Int. Cl.
*G06T 7/62* (2017.01)
*G01N 23/18* (2018.01)
(Continued)

(52) U.S. Cl.
CPC ............... *G06T 7/62* (2017.01); *G01N 23/18* (2013.01); *G01N 23/225* (2013.01);
(Continued)

(58) Field of Classification Search
CPC ..................... G06T 7/62; G06T 7/0004; G06T 2207/10061; G06T 2207/20084;
(Continued)

(56) References Cited

U.S. PATENT DOCUMENTS 6,205,239 B1 * 3/2001 Lin .................. G01N 21/95607
382/209
7,095,022 B2 * 8/2006 Nakasuji ................. H01J 37/06
250/310

(Continued)

FOREIGN PATENT DOCUMENTS

CN 1820346 A 8/2006
JP 2004-363085 A 12/2004
(Continued)

OTHER PUBLICATIONS

International Search Report (PCT/ISA/210) issued in PCT Application No. PCT/JP2019/005648 dated Apr. 2, 2019 with English translation (four (4) pages).

(Continued)

*Primary Examiner* — Hwa Andrew Lee
(74) *Attorney, Agent, or Firm* — Crowell & Moring LLP

(57) ABSTRACT

The present disclosure relates to a system and a non-transitory computer-readable medium for estimating the height of foreign matter, etc. adhering to a sample. In order to achieve the abovementioned purpose, proposed is a system, etc. in which data acquired by a charged particle beam device or features extracted from the data are input to a learning model, which is provided with, in an intermediate layer thereof, a parameter learned using teacher data having data acquired by the charged particle beam device or features extracted from the data as inputs and having the heights (Continued)

or depths of the structures of samples or of foreign matter on the samples as outputs, and height or depth information is output.

11 Claims, 22 Drawing Sheets

(51) Int. Cl.

| | |
|---|---|
| *G01N 23/225* | (2018.01) |
| *G06T 7/00* | (2017.01) |
| *G06T 7/70* | (2017.01) |
| *G06V 10/44* | (2022.01) |
| *G06V 10/764* | (2022.01) |
| *G06V 10/82* | (2022.01) |
| *G06V 20/69* | (2022.01) |
| *H01L 21/66* | (2006.01) |
| *G01N 33/00* | (2006.01) |

(52) U.S. Cl.

CPC .............. *G06T 7/0004* (2013.01); *G06T 7/70* (2017.01); *G06V 10/454* (2022.01); *G06V 10/764* (2022.01); *G06V 10/82* (2022.01); *G06V 20/69* (2022.01); *H01L 22/12* (2013.01); *G01N 33/0078* (2024.05); *G01N 2223/418* (2013.01); *G01N 2223/6116* (2013.01); *G01N 2223/652* (2013.01); *G06T 2207/10061* (2013.01); *G06T 2207/20084* (2013.01); *G06T 2207/30148* (2013.01)

(58) Field of Classification Search

CPC .......... G06T 2207/30148; G01N 23/18; G01N 2033/0078; G01N 2223/418; G01N 2223/6116; G01N 2223/652; G06V 10/454; G06V 10/764; G06V 10/82; G06V 20/69; H01L 22/12; H01J 2237/24578; H01J 2237/2814; H01J 2237/2817

See application file for complete search history.

(56) References Cited

U.S. PATENT DOCUMENTS

| | | | | |
|---|---|---|---|---|
| 7,408,155 | B2 | 8/2008 | Oosaki et al. | |
| 2005/0045821 | A1 | 3/2005 | Noji et al. | |
| 2006/0108525 | A1* | 5/2006 | Nakagaki ................ | H01J 37/28 |
| | | | | 250/310 |
| 2017/0177997 | A1* | 6/2017 | Karlinsky ................ | G06N 3/08 |
| 2018/0106732 | A1 | 4/2018 | Plihal et al. | |
| 2018/0107928 | A1 | 4/2018 | Zhang et al. | |
| 2018/0240225 | A1 | 8/2018 | Harada et al. | |
| 2019/0004504 | A1 | 1/2019 | Yati | |
| 2022/0028052 | A1* | 1/2022 | Li ........................... | G03F 7/705 |

FOREIGN PATENT DOCUMENTS

| | | | |
|---|---|---|---|
| JP | 2006-93251 | A | 4/2006 |
| JP | 2012-173017 | A | 9/2012 |
| TW | 201432252 | A | 8/2014 |
| TW | 201816670 | A | 5/2018 |
| TW | 201825883 | A | 7/2018 |
| TW | 201905731 | A | 2/2019 |
| WO | WO 2014/091928 | A1 | 6/2014 |

OTHER PUBLICATIONS

Japanese-language Written Opinion (PCT/ISA/237) issued in PCT Application No. PCT/JP2019/005648 dated Apr. 2, 2019 (five (5) pages).

Taiwanese-language Office Action issued in Taiwanese Application No. 109103331 dated Mar. 31, 2021 (three (3) pages).

Taiwanese-language Notice of Allowance issued in Taiwanese Application No. 110136681 dated Jul. 28, 2022 (four (4) pages).

\* cited by examiner

```
                    START

ACQUIRE DATA FROM CHARGED        (S101)
        PARTICLE BEAM DEVICE

READ OUT LEARNING MODEL ACCORDING  (S102)
        TO DATA OR FEATURE AMOUNT

INPUT DATA OR FEATURE AMOUNT      (S103)
        TO READ-OUT LEARNING MODEL

OUTPUT HEIGHT INFORMATION         (S104)
        OR DEPTH INFORMATION

END
```

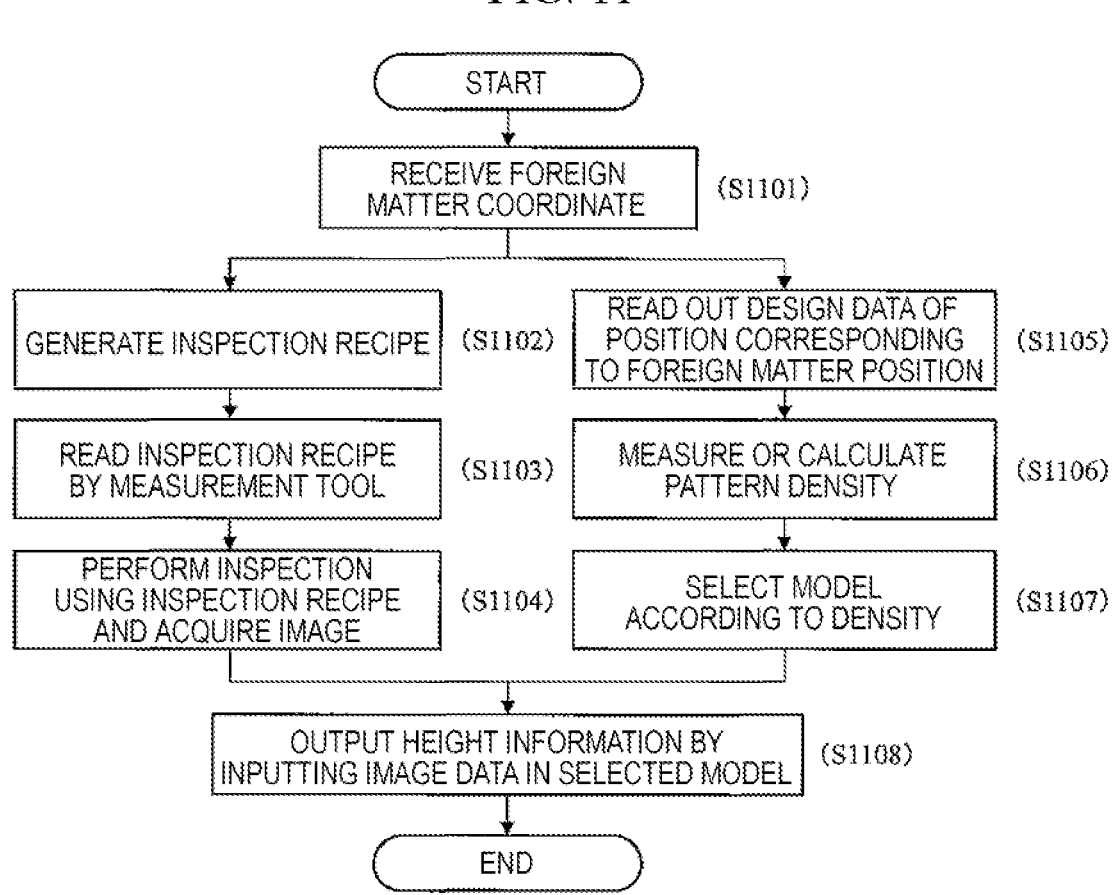

START

RECEIVE FOREIGN MATTER COORDINATE    (S1101)

GENERATE INSPECTION RECIPE    (S1102)

READ OUT DESIGN DATA OF POSITION CORRESPONDING TO FOREIGN MATTER POSITION    (S1105)

READ INSPECTION RECIPE BY MEASUREMENT TOOL    (S1103)

MEASURE OR CALCULATE PATTERN DENSITY    (S1106)

PERFORM INSPECTION USING INSPECTION RECIPE AND ACQUIRE IMAGE    (S1104)

SELECT MODEL ACCORDING TO DENSITY    (S1107)

OUTPUT HEIGHT INFORMATION BY INPUTTING IMAGE DATA IN SELECTED MODEL    (S1108)

END

FIG. 12

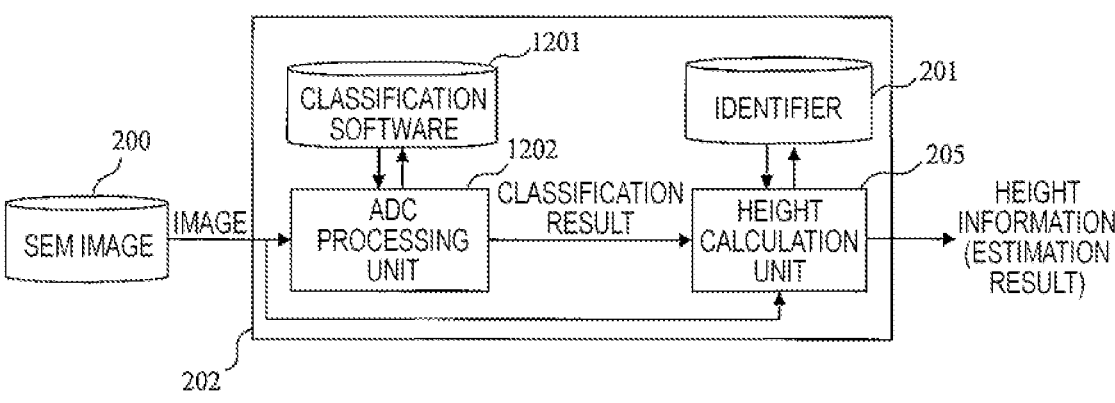

SEM IMAGE    200

CLASSIFICATION SOFTWARE    1201

IDENTIFIER    201

IMAGE

ADC PROCESSING UNIT    1202

CLASSIFICATION RESULT

HEIGHT CALCULATION UNIT    205

HEIGHT INFORMATION (ESTIMATION RESULT)

| 1301 | 1302 | 1303 | 1304 | 1305 | 1306 |
| ID | SEM image | height | accuracy | coordinate | AFM |
| --- | --- | --- | --- | --- | --- |
| A | XXXXXX | | | | ☐ |
| B | XXXXXX | | | | ☑ |
| C | XXXXXX | | | | ☐ |
| D | XXXXXX | | | | ☑ |
| E | XXXXXX | | | | ☐ |
| F | XXXXXX | | | | ☐ |

FIG. 14

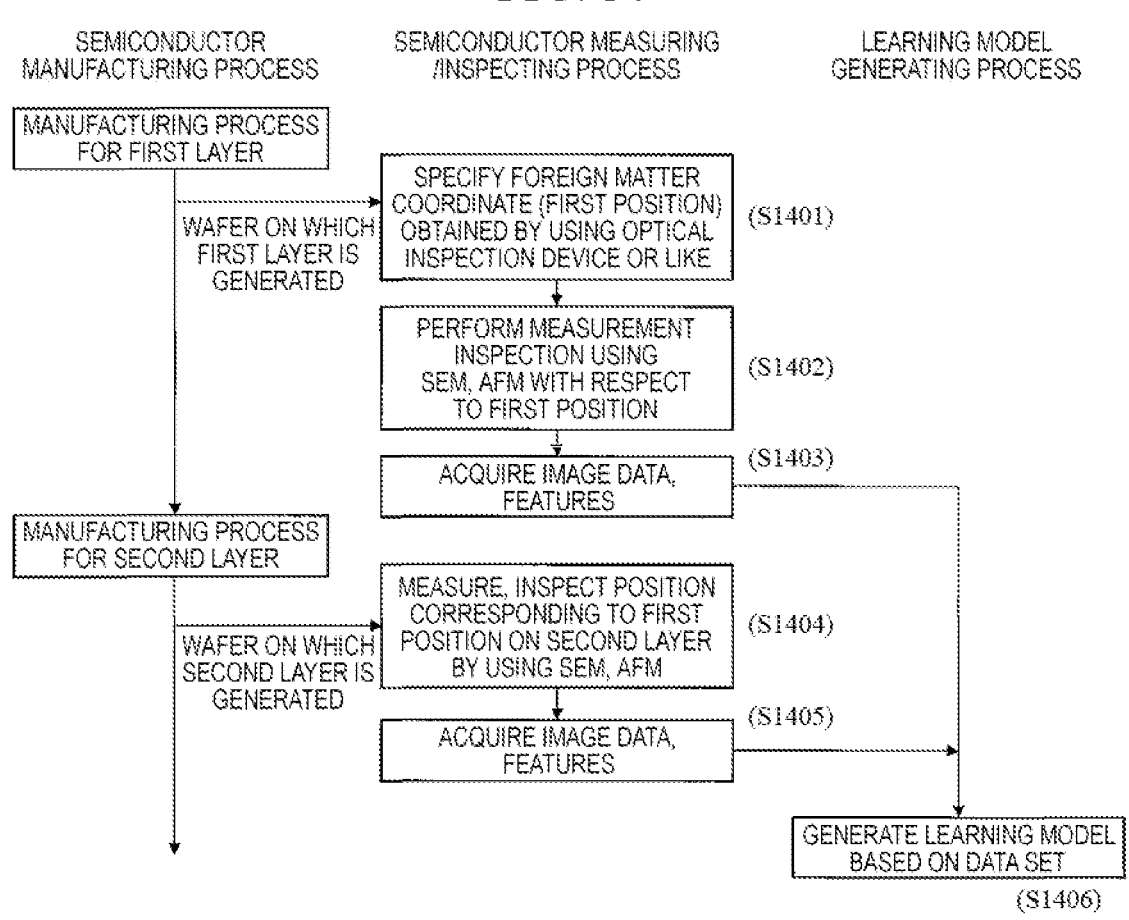

SEMICONDUCTOR
MANUFACTURING PROCESS

SEMICONDUCTOR MEASURING
/INSPECTING PROCESS

LEARNING MODEL
GENERATING PROCESS

MANUFACTURING PROCESS
FOR FIRST LAYER

WAFER ON WHICH
FIRST LAYER IS
GENERATED

SPECIFY FOREIGN MATTER
COORDINATE (FIRST POSITION)
OBTAINED BY USING OPTICAL
INSPECTION DEVICE OR LIKE     (S1401)

PERFORM MEASUREMENT
INSPECTION USING
SEM, AFM WITH RESPECT
TO FIRST POSITION     (S1402)

ACQUIRE IMAGE DATA,
FEATURES     (S1403)

MANUFACTURING PROCESS
FOR SECOND LAYER

WAFER ON WHICH
SECOND LAYER IS
GENERATED

MEASURE, INSPECT POSITION
CORRESPONDING TO FIRST
POSITION ON SECOND LAYER
BY USING SEM, AFM     (S1404)

ACQUIRE IMAGE DATA,
FEATURES     (S1405)

GENERATE LEARNING MODEL
BASED ON DATA SET (S1406)

FIG. 15

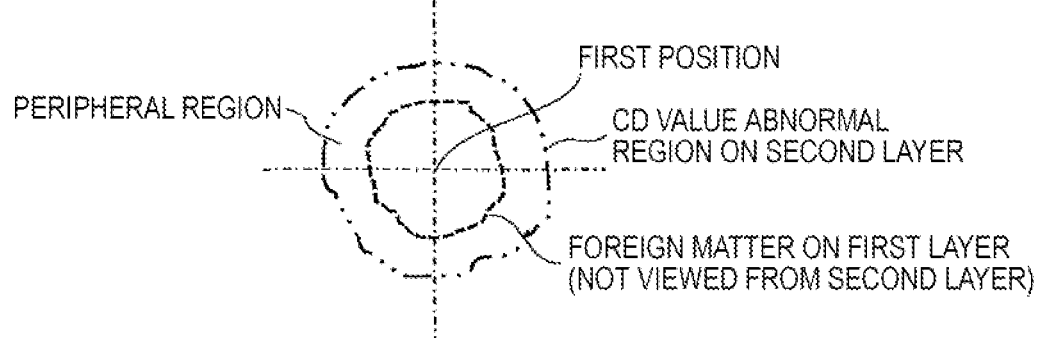

FIRST POSITION

PERIPHERAL REGION

CD VALUE ABNORMAL
REGION ON SECOND LAYER

FOREIGN MATTER ON FIRST LAYER
(NOT VIEWED FROM SECOND LAYER)

FIG. 16

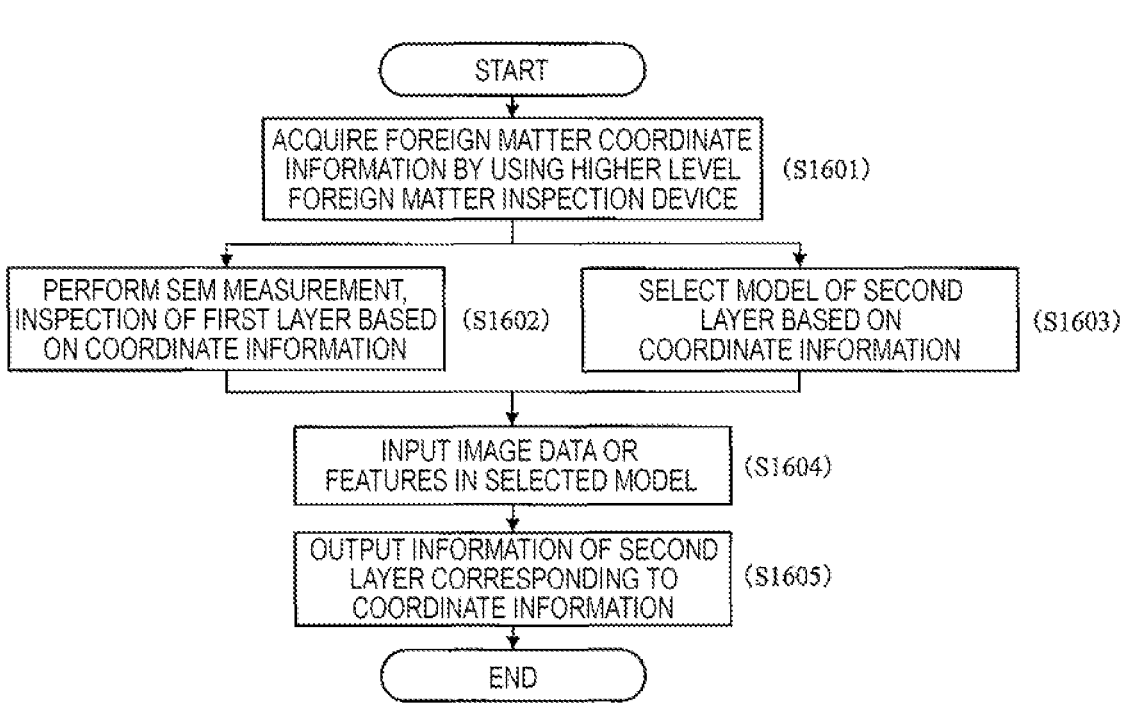

START

ACQUIRE FOREIGN MATTER COORDINATE INFORMATION BY USING HIGHER LEVEL FOREIGN MATTER INSPECTION DEVICE    (S1601)

PERFORM SEM MEASUREMENT, INSPECTION OF FIRST LAYER BASED ON COORDINATE INFORMATION    (S1602)

SELECT MODEL OF SECOND LAYER BASED ON COORDINATE INFORMATION    (S1603)

INPUT IMAGE DATA OR FEATURES IN SELECTED MODEL    (S1604)

OUTPUT INFORMATION OF SECOND LAYER CORRESPONDING TO COORDINATE INFORMATION    (S1605)

END

FIG. 17

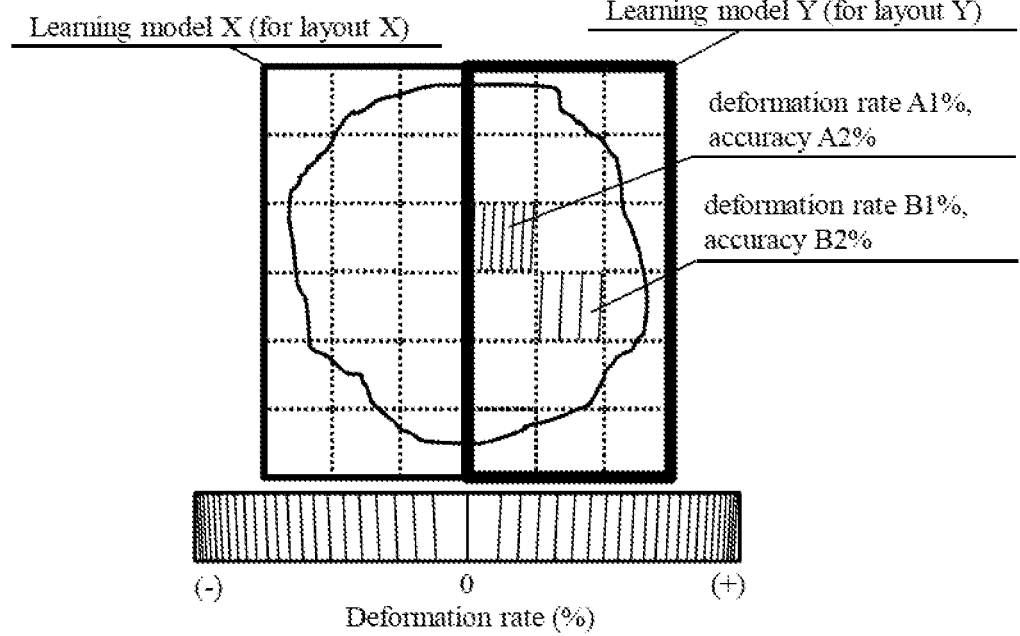

Learning model X (for layout X)

Learning model Y (for layout Y)

deformation rate A1%, accuracy A2% deformation rate B1%, accuracy B2%

(-)                    0                    (+)

Deformation rate (%)

Defect rate:
· Model C1: c1% (accuracy C2%)
· Model D1: dd% (accuracy D2%)

Defect rate:
· Model C1: c2% (accuracy C3%)
· Model E1: ee% (accuracy E2%)

1801

1802 height x1, accuracy y1% height x2, accuracy y2%

FOREIGN MATTER height x3, accuracy y3% height x5, accuracy y5% height x4, accuracy y4%

(a1) IMAGE GENERATION BASED ON OUTPUT OF LEFT-SIDE DETECTOR (a2) IMAGE GENERATION BASED ON OUTPUT OF LEFT-SIDE DETECTOR

HIGH BRIGHTNESS REGION (b) SUBTRACTION (COMPARISON) PROCESSING

Th < DIFFERENCE    Th < DIFFERENCE?    Th ≥ DIFFERENCE (c1) HEIGHT MEASUREMENT USING AFM (c2) ESTIMATING PROCESS BASED ON CALCULATING PROCESS (d) UPDATE OF LEARNING MODEL

FIG. 27

STRUCTURE ESTIMATION SYSTEM AND STRUCTURE ESTIMATION PROGRAM FOR ESTIMATING HEIGHT OF STRUCTURE BASED ON DATA FROM CHARGED PARTICLE BEAM DEVICE

TECHNICAL FIELD

The present disclosure relates to a system and program for estimating a structure of a sample or a foreign matter on the sample.

BACKGROUND ART

There is known a method of measuring a height of a pattern on a sample based on a signal waveform obtained by scanning an electron beam on the sample. JP-A-2006-093251 (Corresponding U.S. Pat. No. 7,408,155) (PTL 1) discloses a method of estimating a cross-sectional shape of a pattern by preparing, in advance, a library that stores cross-sectional shape information of the pattern obtained by an atomic force microscope (AFM) and a signal waveform obtained by scanning with an electron beam in association with each other and referring to the library by using the signal waveform obtained by the beam scanning.

CITATION LIST

Patent Literature

PTL 1: JP-A-2006-093251 (Corresponding U.S. Pat. No. 7,408,155)

SUMMARY OF INVENTION

Technical Problem

With the recent increase in the number of layers of semiconductor devices, in some cases, it is considered that it is necessary to evaluate three-dimensional information such as the height of the foreign matter adhering to the semiconductor device. This is because there is a possibility that adhering of the foreign matter to the sample influences the subsequent manufacturing process. In particular, since a degree of influence on the subsequent process changes according to a difference in the height of the foreign matter, it is preferable to grasp the degree of influence in advance by quantitatively evaluating the height of the foreign matter. On the other hand, as a height measurement device, there is a device such as a cross-sectional scanning electron microscope (SEM) and the AFM as in PTL 1, but measurement of the height for each foreign matter by using the AFM or the like is not realistic in semiconductor measurement in which high throughput is required.

By preparing a library in advance as disclosed in PTL 1, it is possible to suppress the labor of the AFM measurement for each foreign matter. However, unlike the pattern formed on the semiconductor device, there are various shapes and compositions with respect to the foreign matter unintentionally adhering to the wafer, and thus, it is difficult to generate a library as disclosed in PTL 1. In addition, it is considered that a simpler and more accurate height measurement is required for a structure such as a semiconductor pattern.

The present disclosure provides a structure estimation system and program capable of estimating three-dimensional information of an object having various shapes such as a foreign matter and more accurate three-dimensional information than that of other structures.

Solution to Problem

The structure estimation system according to the present disclosure includes a learning device that outputs estimation results such as the structure on the sample, the foreign matter on the structure, and the influence of the foreign matter on another layer on the structure. The learning device performs learning in advance by teacher data in which the data obtained from the charged particle beam device or the feature of the data is set as an input and the estimation result is set as an output. The structure estimation system obtains the estimation result by inputting the data obtained from the charged particle beam device or the feature of the data to the learning device.

Advantageous Effects of Invention

According to the structure estimation system according to the present disclosure, highly accurate three-dimensional information such as a three-dimensional structure, the foreign matter, and influence of the foreign matter can be estimated.

BRIEF DESCRIPTION OF DRAWINGS

FIG. 6 is a schematic configuration diagram of an imaging unit 301 according to a second embodiment.

FIG. 8 is a configuration diagram of a computer system 202 according to the second embodiment.

FIG. 11 is a flowchart illustrating a process in which the foreign matter height estimation system 1000 estimates a height of the foreign matter.

FIG. 12 is a configuration diagram of a computer system 202 using a model according to the ADC result.

FIG. 13 is a diagram illustrating an example of a display screen that displays both height estimation result using the learning model and estimated accuracy output from a learning model.

FIG. 14 is a flowchart illustrating a process of generating a learning model of an identifier 201 in a fifth embodiment.

FIG. 15 is a diagram illustrating a behavior in which the foreign matter placed on a first layer pushes up a second layer.

FIG. 16 is a flowchart illustrating a process of estimating sample information by using the learning model generated as described above.

FIG. 17 is a diagram illustrating a display example of output data (estimation information).

FIG. 27 is a diagram illustrating an example of a computer system 202 including a module (identifier 201) including the estimation model as described above.

DESCRIPTION OF EMBODIMENTS

First Embodiment

Figure 1:
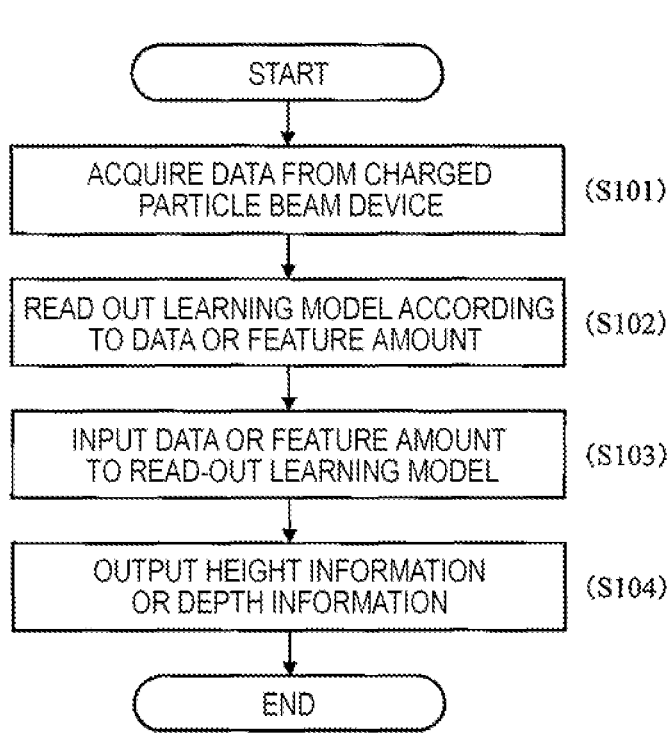
FIG. 1 is a flowchart illustrating an outline of the structure estimating method according to a first embodiment.

FIG. 1 is a flowchart illustrating an outline of a structure estimating method according to a first embodiment of the present disclosure. In the first embodiment, a height and a depth of a structure (in the case of a semiconductor wafer, the structure is a convex pattern such as a line or a pillar, a concave pattern such as a hole or a trench, or the like) formed on a sample or a foreign matter or the like placed on the sample are estimated from data (observation image) obtained by a charged particle beam device such as a scanning electron microscope.

The data is acquired from the charged particle beam device (S101), a learning model according to the acquired data or a feature amount extracted from the data is read out (S102), the data or the feature amount is input to the read-out learning model (S103), and information about the height or depth of the structure or the foreign matter is output (S104).

It is possible to acquire brightness, dimension information, a shadow image, and the like of the structure and the foreign matter from the data acquired by the scanning electron microscope or the like. In particular, there is a correlation between the brightness of the bottom of the concave pattern and the depth of the concave pattern, and furthermore, there is also a correlation between a width and a size of the concave pattern and the depth of the concave pattern. Hereinafter, a depth measurement system for measuring (estimating) the depth of the pattern or the like formed on the sample will be described with reference to the drawings.

Figure 2:
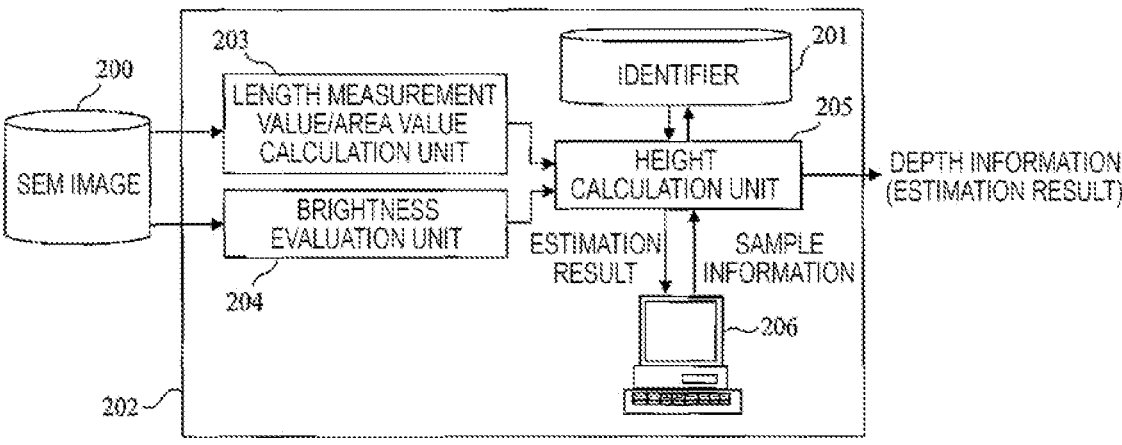
FIG. 2 is a diagram illustrating an example of a computer system 202 according to the first embodiment.

FIG. 2 is a diagram illustrating an example of a computer system 202 according to the first embodiment. The computer system 202 estimates the height of the structure and the foreign matter on the sample by inputting the observation image of the sample to the learning model. With respect to teacher data of the learning model, the image generated by an image generating device such as an electron microscope or the feature amount extracted from the image is used as an input, and the height of the structure or the foreign matter on the sample is used as an output.

The computer system 202 includes an identifier 201, a length measurement value/area value calculation unit 203, a brightness evaluation unit 204, a height calculation unit 205, and an input/output device 206. A SEM image 200 is the observation image of the sample acquired by the charged particle beam device. The length measurement value/area value calculation unit 203 acquires a dimension value and an area value of the sample from the SEM image 200. The brightness evaluation unit 204 acquires the brightness value of the SEM image 200. The input/output device 206 is a device for allowing a user to input information about a material and the like of the sample (described again in FIG. 4 later). The height calculation unit 205 estimates information about the height or depth of the structure or the foreign matter on the sample by inputting the brightness value/the dimension value/the area value/the sample information to the identifier 201.

As the identifier 201, an identifier on which a learning process using the teacher data is performed is used so as to output a depth level corresponding to the observation image of the sample or the feature amount extracted from the observation image. As the identifier 201, any learning device such as a neural network, a regression tree, or a Bayesian identifier can be used. The learned model data can be stored in a storage unit 305 described later.

Figure 3:
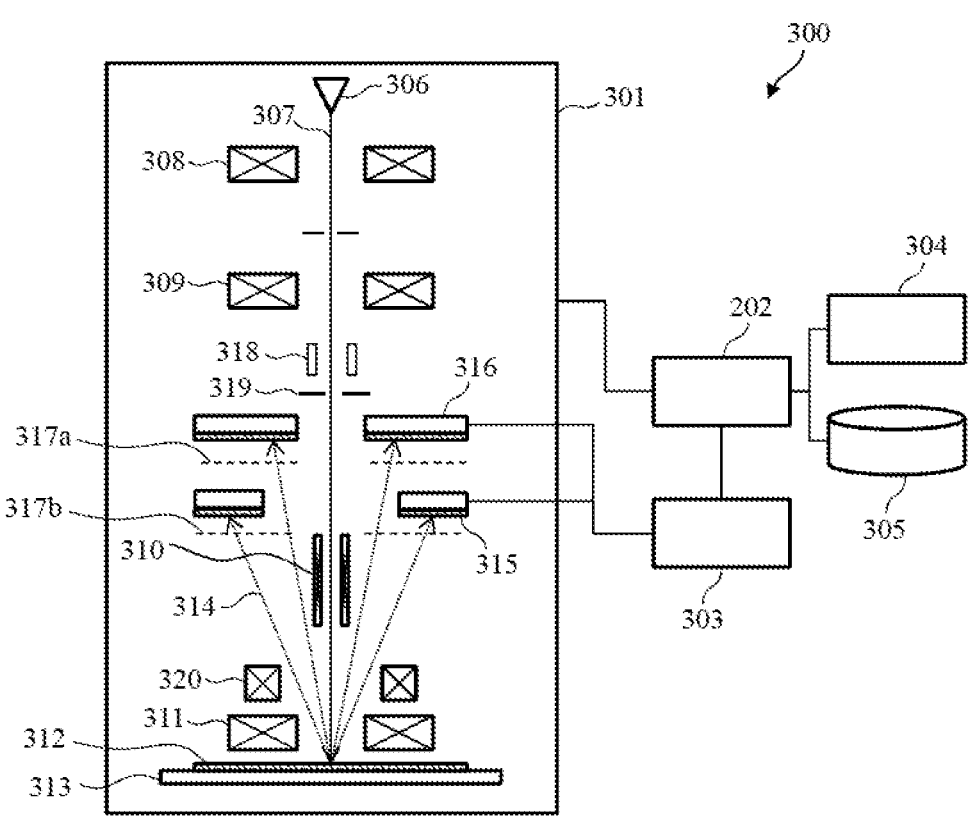
FIG. 3 is a diagram illustrating an example of a depth (height) measurement system 300.

FIG. 3 is a diagram illustrating an example of a depth (height) measurement system 300. The depth measurement system 300 includes an imaging unit 301, a computer system 202, a signal processing unit 303, an input/output unit 304, and the storage unit 305. In addition to performing the depth estimation described with reference to FIG. 2, the computer system 202 controls the following optical system included in the imaging unit 301.

The imaging unit 301 includes an electron gun 306 that performs irradiation with an electron beam 307, a focusing lens 308 that focuses the electron beam 307, and a focusing lens 309 that further focuses the electron beam 307 having passed through the focusing lens 308. Furthermore, the imaging unit 301 includes a deflector 310 that deflects the electron beam 307 and an objective lens 311 that controls a focusing height of the electron beam 307.

A sample 312 placed on a sample stage 313 is irradiated with the electron beam 307 that has passed through the optical system of the imaging unit 301. Emitted electrons 314 such as secondary electrons (SE) and backscattered electrons (BSE) emitted from the sample 312 by the irradiation with the electron beam 307 are detected by a lower detector 315 and an upper detector 316 installed in the trajectory. An opening provided in the upper detector 316 is for passing the electron beam 307. By forming the opening to be sufficiently small, the secondary electrons emitted from the bottoms of deep holes and deep grooves formed on the sample 312, passing near the center of the pattern, and escaping on the sample surface can be detected. The emitted electrons 314 can be determined in terms of energy by performing energy filtering by using an energy filter 317a immediately before the upper detector 316 or an energy filter 317b immediately before the lower detector 315.

The imaging unit 301 further includes a blanking deflector 318 that restricts the electron beam 307 from reaching the sample 312 by deflecting the electron beam 307 off the optical axis and a blanking electrode 319 that receives the electron beam 307 deflected by the blanking deflector 318.

The signal processing unit 303 generates the SEM image 200 based on the output of the lower detector 315 and the output of the upper detector 316. The signal processing unit 303 generates the image data by storing a detection signal in a frame memory or the like in synchronization with scanning of a scanning deflector (not illustrated). In the case of storing the detection signal in the frame memory, a signal profile (one-dimensional information) and the SEM image (two-dimensional information) are generated by storing the detection signal at a position corresponding to a scanning position of the frame memory. In addition, the secondary electrons passing near the optical axis escaped from the deep hole or the like are guided outside the opening of the lower detector 315 (detection surface of the lower detector 315) by deflecting the secondary electrons with the deflector 320 as necessary.

Figure 4:
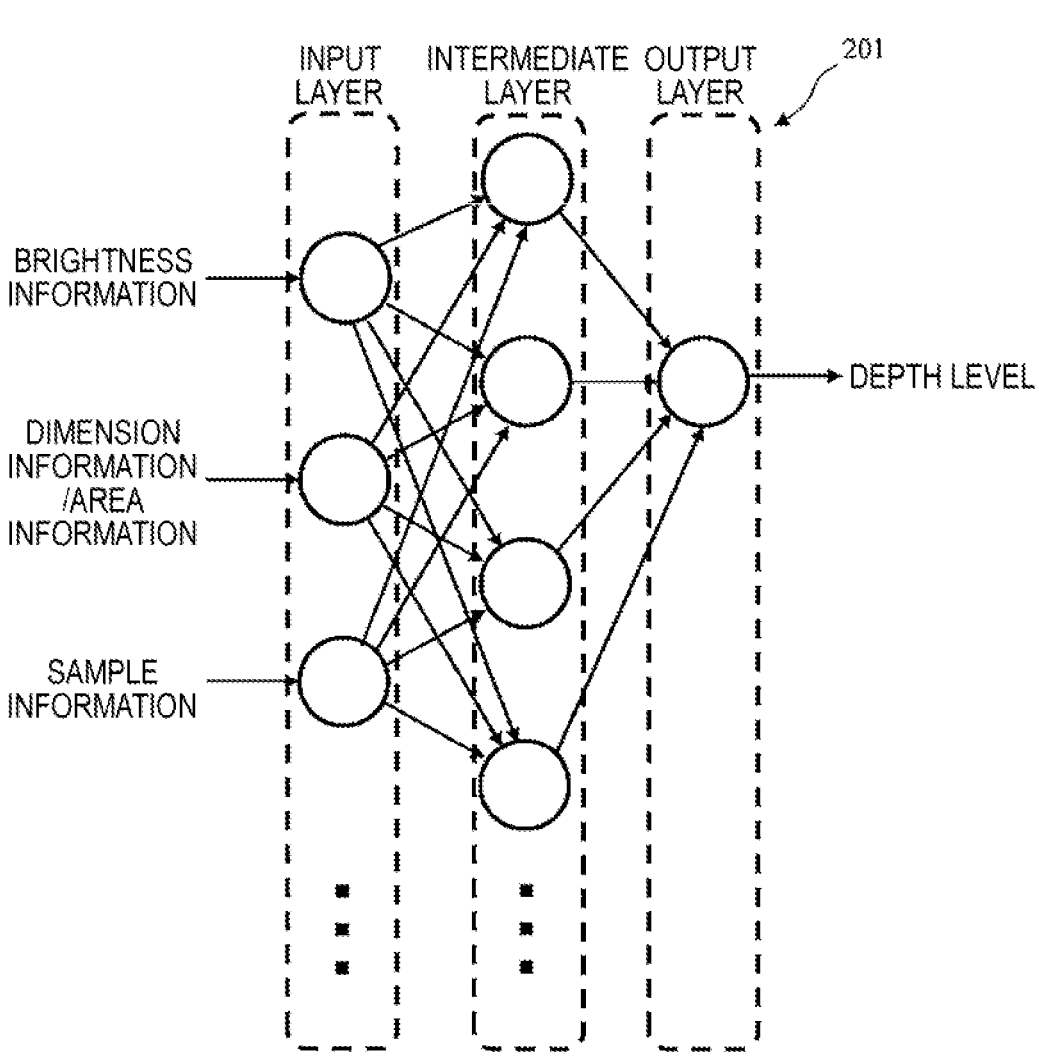
FIG. 4 is a diagram illustrating a configuration example of an identifier 201.

FIG. 4 is a diagram illustrating a configuration example of the identifier 201. Herein, an example has been described in which the identifier 201 is configured by using a neural network, but the present invention is not limited thereto, and other identifiers can also be used. The identifier 201 includes an input unit for inputting (a) brightness information at a bottom of a hole or a trench and (b) dimension information or area information of the hole or the trench as an input layer. In addition, since the brightness of the bottom of the pattern depends on the secondary electron emission efficiency 6 of the material constituting the bottom, for example, an input unit for inputting information about the material of the bottom as the sample information may be provided. The material information includes, for example, the type of material, the secondary electron emission efficiency 6, and the like.

The neural network outputs the depth level from the output layer by sequentially propagating the information input to the input layer as an intermediate layer=>an output layer. The intermediate layer is configured with a plurality of intermediate units. The information input to the input layer is weighted by a coupling coefficient between each input unit and each intermediate unit and input to each intermediate unit. The value of the intermediate unit is obtained by adding the input to the intermediate unit. The value of the intermediate unit is non-linearly transformed by an input/output function. The output of the intermediate units is weighted by the coupling coefficient between each intermediate unit and each output unit and is input to each output unit. The output value of the output layer is obtained by adding the input to the output unit. The identifier 201 outputs a parameter that represents the value that can be expressed in SI unit (for example, micrometer) and other degrees of depth. Instead of or in combination with the parameter, the estimation result of whether the value is deeper or shallower than a certain reference value may be output.

By advancing the learning, the parameter (constant, a coefficient, or the like) such as a coupling coefficient between the units and a coefficient that represents the input/output function of each unit is gradually optimized. The storage unit 305 stores the optimized value as the learning result of the neural network. Similarly, when the identifier 201 other than the neural network is used, the storage unit 305 stores the parameter optimized in the learning process. The same applies to the following embodiments.

In the above-mentioned example, an example has been described in which dimension information or area information and brightness information of the bottom are extracted and used as the feature amounts as the input data of the identifier 201. When deep learning is used, the feature amount can be automatically discovered and learned from observation images.

Figure 5:
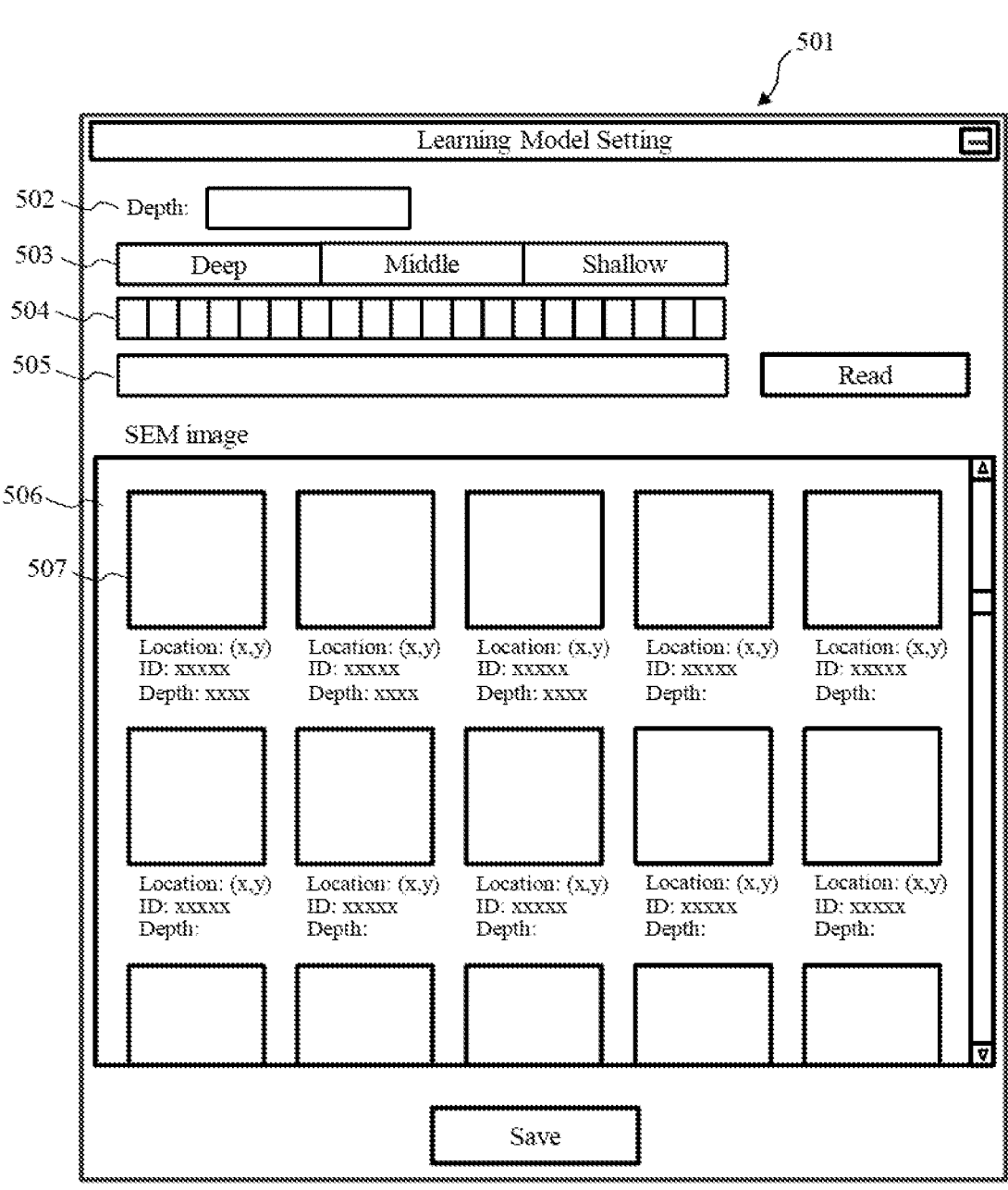
FIG. 5 is a diagram illustrating an example of a GUI screen 501 for generating a learning model.

FIG. 5 is a diagram illustrating an example of a GUI screen 501 for generating the learning model. The user can construct a learning model of the identifier 201 (learn the identifier 201) by using the GUI screen 501. The GUI screen 501 is displayed on the display device included in the input/output device 206 of FIG. 2. The user constructs a learning model by inputting a depth of an empirically known pattern or a height measurement result by another depth (height) measurement device as the teacher data on the GUI screen 501.

A SEM image display field 506 displays a SEM image 507 stored in a predetermined storage medium in association with coordinates (location) and the identifier (ID) on the sample. The learning model can be constructed by selecting an arbitrary image from the SEM image display field 506 and inputting necessary information from the input units 502 to 505.

When the depth is specifically known by analysis by another analyzing device, the value is input to the input unit 502 as correct answer data of the image. By repeating the inputting, A learning phase of deep learning can be performed. The input unit 503 is provided with a button indicating the degree of depth. In FIG. 5, a button indicating three levels of deep, middle, and shallow is illustrated. When the degree of depth is roughly known, the correct answer data is selected by using the input unit 503. When the depth information is determined in more detail than the classification of the input unit 503, the input unit 504 is provided so as to select a button according to the depth as the correct answer data. The input unit 505 is provided to input and read out the address (URI, or the like) of the storage medium which stores the height information in order to read out the height information acquired by another height measurement device and register the height information as the correct answer data. The read-out depth information is used as the correct answer data for the image of which coordinates and identifiers match, and the teacher data together with the image data is automatically generated.

As the imaging unit 301, a scanning electron microscope (cross section SEM) that generates the image obtained by scanning the exposed surface of the sample of which cross section is exposed with a focused ion beam or the like with the electron beam or an atomic force microscope or the like that can measure the height with high accuracy can be used. By storing the depth (height) information obtained by these devices together with the coordinate information and the identification information of the pattern, it is possible to prepare information for constructing the learning model in advance. In the case of measuring the depth with the cross-sectional SEM, it is considered that the depth is measured by preparing a couponed sample so that the cross sections of the plurality of patterns having different heights are exposed and performing the SEM observation.

Second Embodiment

In the first embodiment, an example has been described in which the measurement of the depth is for the pattern constituting a semiconductor device such as a via or a trench. In a second embodiment of the present disclosure, a system for estimating the height of the foreign matter unintentionally adhering to the sample by using the image obtained by an image forming device such as a scanning electron microscope will be described.

When the foreign matter adheres to the semiconductor wafer, there is a possibility that the foreign matter influences the subsequent manufacturing process. In particular, since the degree of influence on the subsequent process changes according to the difference in the height of the foreign matter, it is preferable to grasp the degree of influence in advance by quantitative evaluation of the height of the foreign matter. On the other hand, although there are devices such as the above-described cross-sectional SEM and the above-described AFM as the height measurement device, the measurement of the height for each foreign matter by using the AFM or the like is not practical in the semiconductor measurement which requires high throughput. Therefore, in the second embodiment, an example is described in which the learning is performed by using the learning data in which the observation image or the feature amount of the observation image is set as an input and the height of the foreign matter is set as an output.

Figure 6:
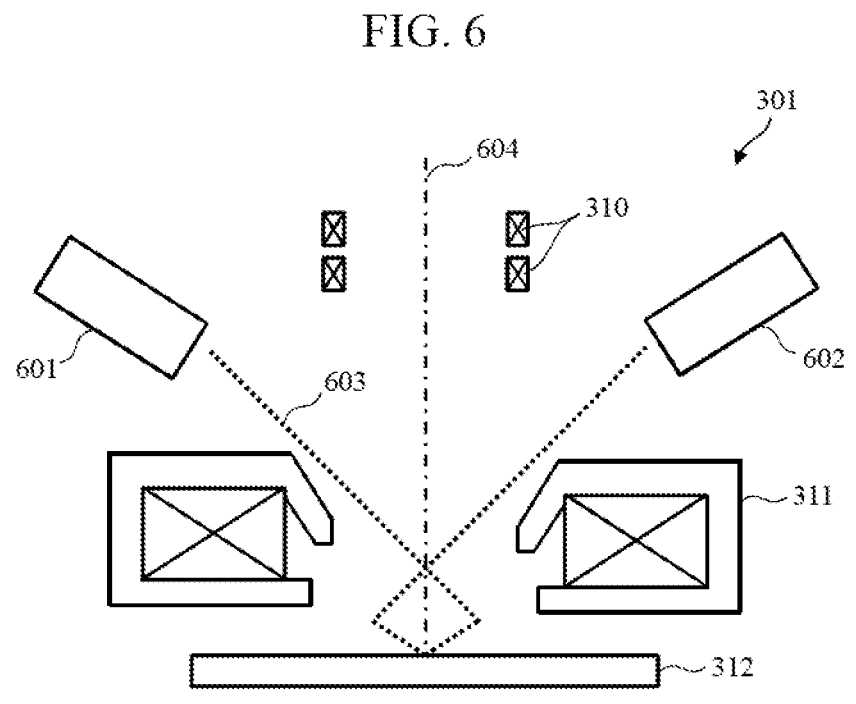

FIG. 6 is a schematic configuration diagram of the imaging unit 301 in the second embodiment. The same configurations as those in FIG. 3 are denoted by the same reference numerals. The configurations other than the imaging unit 301 are the same as those of the first embodiment. The optical system illustrated in FIG. 6 includes detectors 601 and 602. The detectors 601 and 602 detect backscattered electrons (BSE) emitted at relatively large elevation angles among the electrons emitted from the sample 312 based on the irradiation of the beam scanned by the deflector 310. FIG. 6 illustrates an example in which two detectors on the left and right are provided axis-symmetrically on an ideal optical axis 604 of the beam, but two detectors are further arranged in a vertical direction of the paper surface, so that a four-directional detector may be configured.

In the second embodiment, a scanning electron microscope provided with two or four detectors as the imaging unit 301 is described, but any of the number of detectors may be used as long as a shadow image of the sample can be formed. The detector is arranged in a direction perpendicular to the ideal optical axis 604. In addition, the detector is arranged at a position where electrons 603 emitted from a direction tilt with respect to the optical axis from the foreign matter or the like due to the focusing operation of the objective lens 311 reach. The signal processing unit 303 can generate the shadow image of the sample by using the detection result by the detectors.

As compared to the image formed based on the detection of general secondary electrons, the image based on the outputs of the shadow image detectors provided in multiple directions becomes an image as the foreign matter or the like is viewed diagonally from the above. Therefore, more information in the height direction is included, and thus, the feature amount in the height direction can be relatively easily extracted. Therefore, in the second embodiment, the learning model is learned by using the teacher data in which the information obtained from the outputs of the detectors arranged in the multiple directions is set as an input and the height information is set as an output. The height information is estimated by inputting the information obtained from the scanning electron microscope including the detectors in the multiple directions to the learning model.

Other methods for viewing the foreign matter diagonally from the above may use (a) the beam tilt in which the irradiation with the beam tilt from a direction tilted with respect to the ideal optical axis 604 is performed by using a beam tilting deflector, and (b) the stage tilt in which the sample stage is tilt and the irradiation with the beam in a tilt direction is performed.

Figure 7:
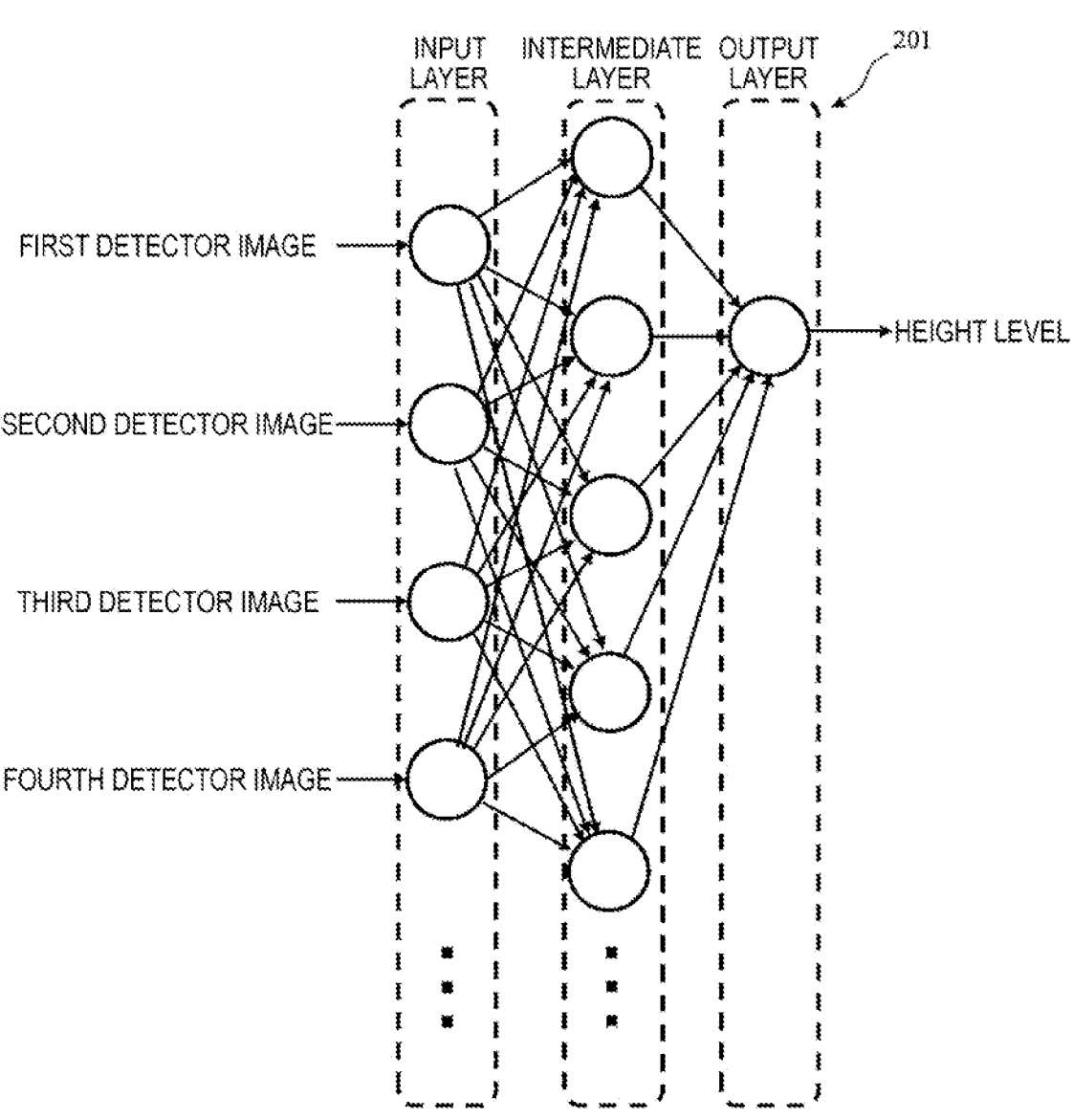
FIG. 7 is a diagram illustrating a configuration example of an identifier 201 according to the second embodiment.

FIG. 7 is a diagram illustrating a configuration example of the identifier 201 according to the second embodiment. In the second embodiment, the input to the height calculation unit 205 is at least one of (a) an output of a multi-directional detector (for example, a 4-direction detector), (b) an image formed based on the output, and (c) a feature amount extracted from the image. FIG. 7 illustrates an example in which the image formed based on the output of each of the four-directional detectors is used as the input data. An energy dispersive X-ray spectrum (EDX) detector may be provided in the scanning electron microscope, and element information obtained by element analysis may be used as the input data. According to the system including the identifier 201 as illustrated in FIG. 7, it is not necessary to frequently measure the height by the cross-sectional SEM or the AFM, and it is possible to estimate the height information of the foreign matter based on the information obtained by the image generating device such as the scanning electron microscope.

Next, the process of generating the learning model will be explained. The input of the teacher data includes at least one of (a) an output of a four-directional detector, (b) an image obtained based on the output, and (c) one or more feature amounts extracted from the image. The output of the teacher data includes the height information obtained from the high accurate height measurement device such as a cross-sectional SEM or the AFM. The learning model is generated by using the teacher data.

As a deep neural network method of generating height map data by the AFM or the like from image data, a semantic segmentating method of converting data in pixel units with a multi-step encoder/decoder using a pooling layer and an image generating method of generating data in pixel unit using hostile generation learning can be applied.

Figure 8:
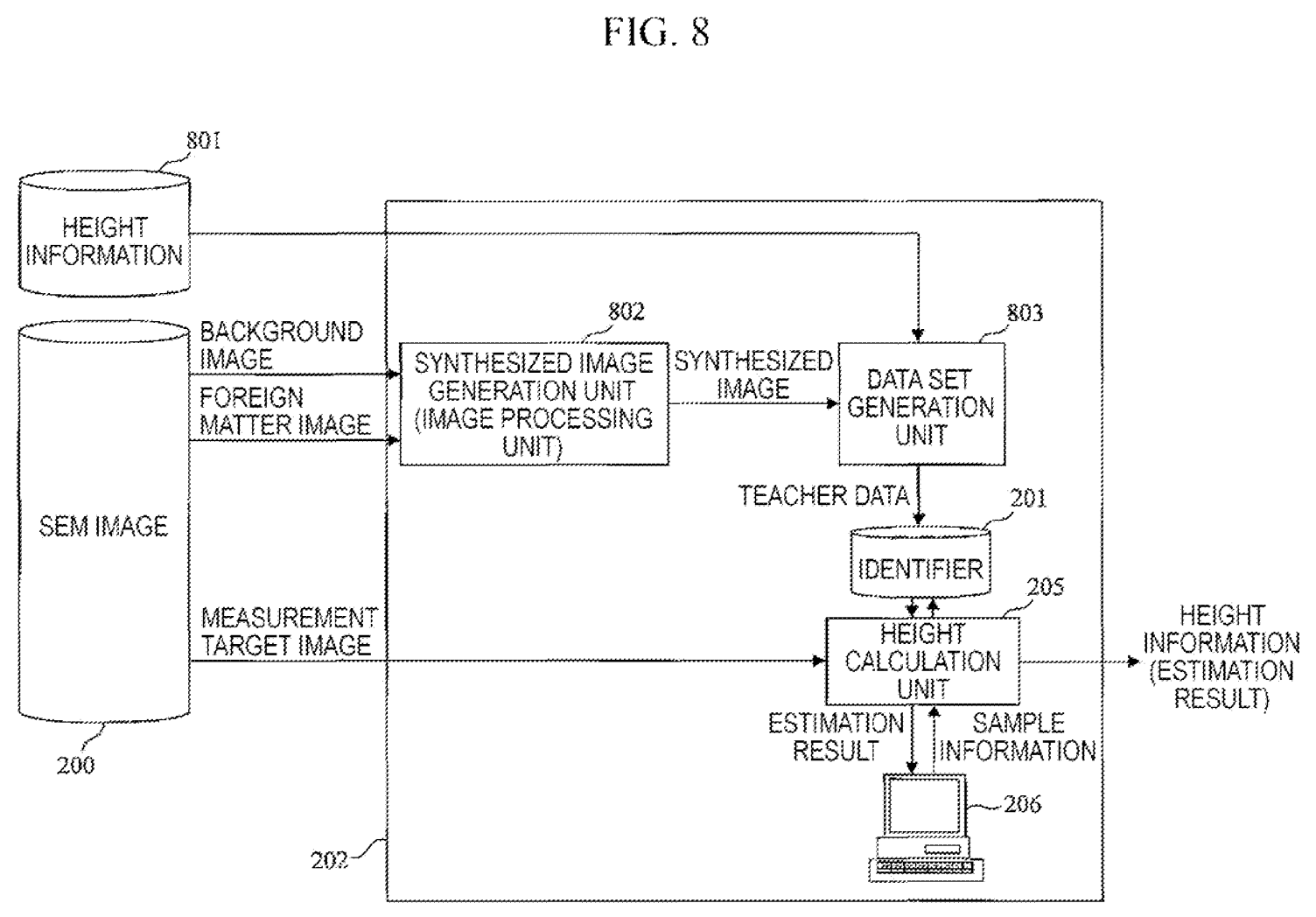

FIG. 8 is a configuration diagram of the computer system 202 according to the second embodiment. In the second embodiment, the computer system 202 includes a synthesized image generation unit 802 and a data set generation unit 803 instead of the length measurement value/area value calculation unit 203 and the brightness evaluation unit 204 described in the first embodiment. The synthesized image generation unit 802 generates the synthesized image by using a background image and the foreign matter image described later. The data set generation unit 803 generates the teacher data by using the synthesized image and height information 801 as a data set.

Figure 9:
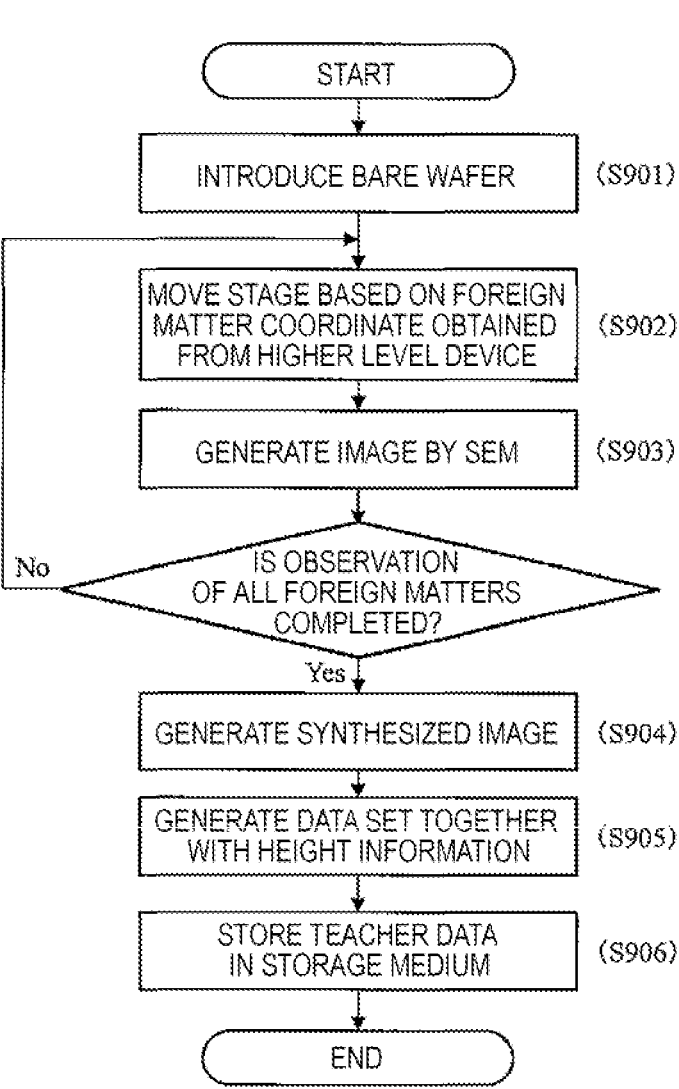
FIG. 9 is a flowchart illustrating a process of generating a learning model based on an output of a scanning electron microscope.

FIG. 9 is a flowchart illustrating a process of generating the learning model based on the output of the scanning electron microscope. Herein, an example of generating the learning model based on the SEM image of the foreign matter adhering to a bare wafer (a wafer on which a pattern is not formed) will be described.

The bare wafer is introduced to the scanning electron microscope (S901), and the stage is moved so that the foreign matter is located in the field of view of the scanning electron microscope based on the foreign matter information obtained from a higher level device such as an optical microscope (S902). Then, the region containing the foreign matter is scanned with the electron beam, and the SEM image 200 is generated based on the signal detected by the four-directional detector (S903). At this time, in order to increase the data amount of the learning model, the plurality of images having different beam conditions such as a focus of an electron beam and an acceleration voltage or different signal processing conditions such as auto brightness contrast control (ABCC) are acquired for one foreign matter. The image together with the coordinate information and the identification information adhering to the foreign matter is stored in the storage unit 305.

The synthesized image generation unit 802 generates the synthesized image for each of different combinations of the plurality of types of the background images acquired in advance and the acquired foreign matter image (S904). The background image is an image of a wafer on which a pattern or the like is formed by a predetermined manufacturing process, and it is assumed that the image is acquired for each of different layouts. In the case of generating the synthesized image, the foreign matter image is generated for each of the layouts by cutting out the foreign matter portion from the foreign matter image on the bare wafer with image processing and superimposing the cut-out portion on the plurality of images prepared as the background images. With respect to the background image, similarly to the foreign matter image, it is preferable to prepare a plurality of types of images obtained for different image acquisition conditions. By acquiring and synthesizing the foreign matter image and the background image separately, it is possible to generate the learning model with a small number of times of image acquisition.

The data set generation unit 803 generates the teacher data by using the height information 801 obtained by the AFM or the cross-sectional SEM and the synthesized image generated by a synthesizing process as a data set (S905) and stores the teacher data in the storage unit 305 (S906). According to the learning model generating method as described above, it is possible to generate the plurality of images to be provided for the learning model from one foreign matter image.

The image may be acquired while the acceleration voltage of the beam, or the like is changed, and the teacher data in which the continuous image (moving image) and the height information are set may be generated. For example, when the image is acquired by changing the acceleration voltage (landing energy) of the beam, the reaching depth of the beam with respect to the foreign matter or a structure of the sample changes. That is, the change in appearance of the foreign matter on the continuous image illustrates different behaviors according to the height of the foreign matter. Therefore, information such as (a) the plurality of images obtained by beam irradiation of each landing energy, (b) a continuous image (moving image) of the plurality of images, or (c) a change in brightness of the foreign matter extracted from the image is acquired by changing the landing energy, and a teacher data set is generated in which the information and the height information obtained by the AFM or the like are set. The height estimation model is generated by using the teacher data. In the height estimation model, the intermediate layer is provided with the parameter learned by using the teacher data in which the data obtained by the charged particle beam device or the feature amount extracted from the data is set as an input and the height of the structure of the sample or the foreign matter on the structure is set as an output. By inputting the output of the scanning electron microscope to the learning model, the height can be estimated with high accuracy. The moving image as the input data may be a continuous image obtained by scanning a plurality of frames without changing conditions such as landing energy.

Third Embodiment

In order to improve the accuracy of the learning model, the imaging conditions (for example, magnification, landing energy, ABCC conditions, a scanning speed of beam, a scanning method, or the like) of the scanning electron microscope, manufacturing process conditions (identification information of a manufacturing process, manufacturing conditions in each manufacturing process, and the like) for a semiconductor device, and information (design data, or the like) of a pattern of a portion where the foreign matters are located may also be used as the input data. In addition, the learning model may be prepared for each information, and the height may be estimated based on the selection of the learning model according to the pattern information around the foreign matter obtained from, for example, the electron microscope image. Due to the change in these conditions, an image quality of the electron microscope is changed, and thus, by using these conditions as the input data or preparing the learning model for each of these conditions, it may be possible to implement a high accuracy of the model. Therefore, in the third embodiment of the present disclosure, an example will be described in which a plurality of the learning models are prepared in advance, an appropriate learning model is selected from among the plurality of the learning models to obtain an estimation result.

Figure 10:
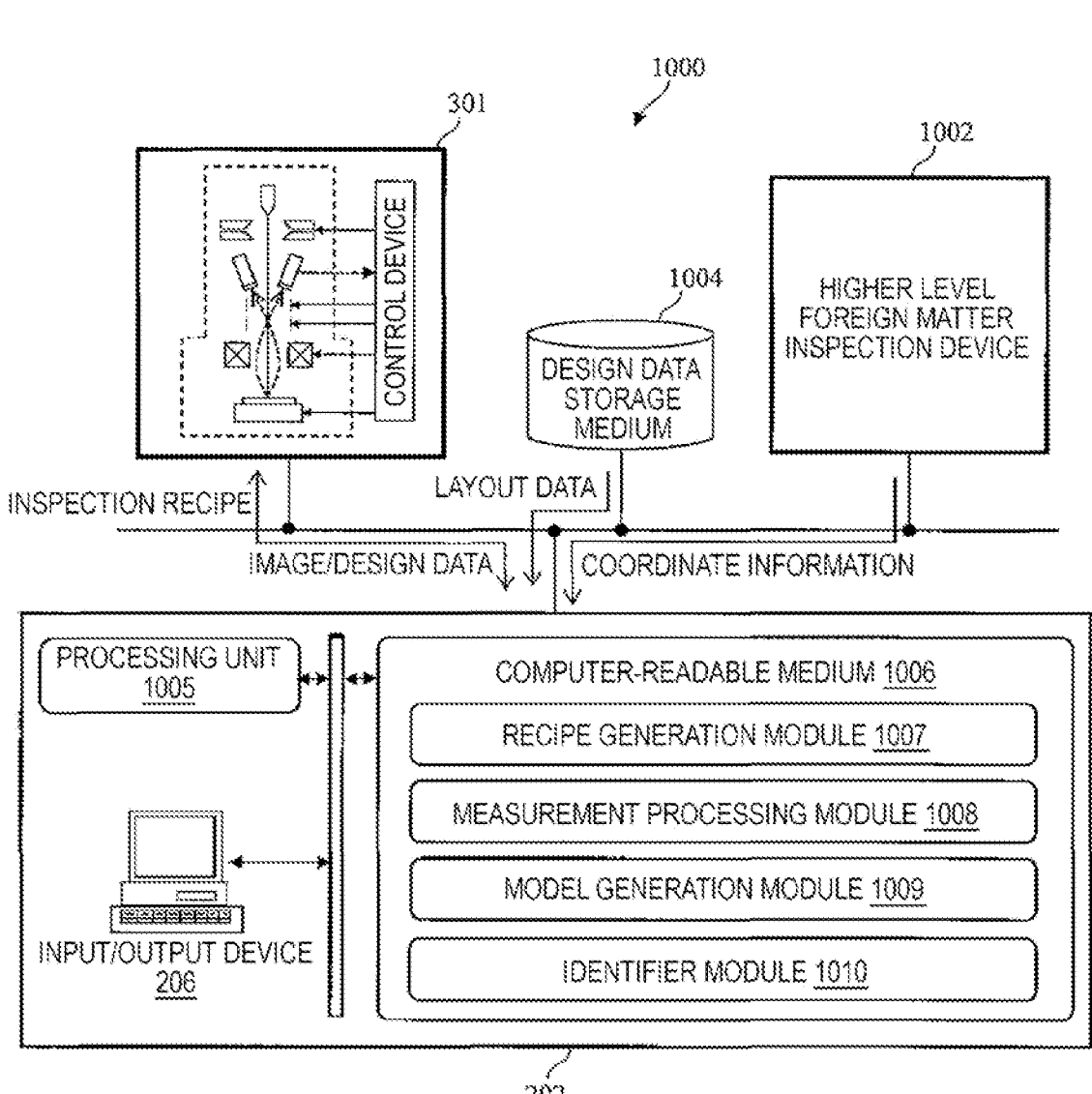
FIG. 10 is a configuration diagram of a foreign matter height estimation system 1000 according to a third embodiment.

FIG. 10 is a configuration diagram of a foreign matter height estimation system 1000 according to the third embodiment. The foreign matter height estimation system 1000 includes an imaging unit 301, a higher level foreign matter inspection device 1002, a storage medium for storing design data 1004, and a computer system 202.

The higher level foreign matter inspection device 1002 is a device, for example, like an optical inspection device that detects reflected light obtained by irradiating the sample with light and detects the coordinates of the foreign matter on the sample from the detected reflected light. A device that detects the coordinates of the foreign matter by another appropriate method can also be used.

The computer system 202 includes a computer-readable medium 1006, a processing unit 1005 that executes each module stored in the computer-readable medium 1006, and an input/output device 206. The computer-readable medium 1006 allows a recipe generation module 1007, a measurement processing module 1008, a model generation module 1009, and an identifier module 1010 to be stored therein. These modules are software modules that realize the functions implemented by each module by being executed by the processing unit 1005. Hereinafter, for the convenience of description, each module may be described as an operating subject, but it is the processing unit 1005 that actually executes each module.

The recipe generation module 1007 automatically operates the imaging unit 301 based on the coordinate information of the foreign matter output by the higher level foreign matter inspection device 1002 and measurement conditions input from the input/output device 206. The measurement processing module 1008 measures the size or the like of the pattern, the foreign matter, or the like according to a predetermined measurement algorithm based on the output of the imaging unit 301. The model generation module 1009 learns the parameter of the intermediate layer of the model by using the teacher data in which the data obtained by the imaging unit 301 (the output image and the like of the four-directional detector described in the second embodiment) is set as an input and the height obtained as a result of the measurement of the height by using the AFM or the like for the foreign matter imaged by the imaging unit 301 is set as an output. The identifier module 1010 implements the identifier 201 that estimates the height by using the learning model learned by the model generation module 1009.

The model generation module 1009 generates a plurality of models according to the pattern state formed on the sample and stores the plurality of models in the computer-readable medium 1006. The output of the four-directional detector is greatly influenced by the pattern state formed on the sample, and in particular, a pattern density is greatly influenced. Therefore, in the third embodiment, the plurality of models are assumed to be stored according to the pattern density. For example, the pattern density is the parameter indicating the degree including the number of patterns per unit area, the number of pattern edges per unit area, an occupied area of patterns per unit area, a pattern length per unit area, and the like. That is, the higher the number of patterns per unit area, the higher the density. Instead of the density, the density of the pattern or other value that changes according to the density may be used.

The identifier module 1010 receives an input to the identifier 201 (input to each input unit) and calculates the output of each unit by using the learning result (the coupling coefficient, the coefficient of the input/output function, or the like) stored in the storage unit 305. The output can be used as the output of the identifier 201. Therefore, the identifier 201 is implemented. The identifier 201 in other embodiments can be similarly implemented.

FIG. 11 is a flowchart illustrating a process in which the foreign matter height estimation system 1000 estimates the height of the foreign matter. The computer system 202 receives the coordinate information of the foreign matter detected by the higher level foreign matter inspection device 1002 (S1101). The processing unit 1005 generates a recipe of the imaging unit 301 based on the information stored in the recipe generation module 1007 (S1102). Specifically, the recipe is generated based on control conditions or the like of the stage such as aligning the field of view of the imaging unit 301 with the foreign matter coordinates acquired by the higher level foreign matter inspection device 1002 and device conditions or the like of the imaging unit 301 input from the input/output device 206 (optical conditions such as an acceleration voltage of the beam and magnification). The imaging unit 301 reads the generated recipe (S1103) and executes inspection by using an inspection recipe (S1104).

On the other hand, the recipe generation module 1007 or the measurement processing module 1008 reads out the design data of the portion corresponding to the received coordinates based on the received coordinate information (S1105) and measures and calculates a value (for example, counting the number of patterns per unit area) related to the pattern density of the foreign matter coordinates (S1106). The identifier module 1010 selects the model according to the pattern density obtained by the measurement or the calculation for the height estimation (S1107) and outputs the height information by inputting the image obtained by the inspection to the selected model (S1108). By the procedure as illustrated in FIG. 11, the height can be estimated based on the selection of an appropriate model according to the position where the foreign matter exists.

In the learning model, the result of auto defect classification (ADC) may be set as the input data, or and the height using the model may be estimated by preparing the model corresponding to the ADC result and selecting an appropriate model according to the ADC result. The ADC is a defect type estimating method using the image processing. The ADC classifies the causes of occurrence of the foreign matter and defect by classification software based on a predetermined rule. An example of using a model according to the classification result will be described below.

FIG. 12 is a configuration diagram of the computer system 202 using the model according to the ADC result. The computer system 202 of FIG. 12 includes an ADC processing unit 1202 that classifies the foreign matters and the defects included in the SEM image 200 by reading the classification software 1201 into. The identifier 201 includes the learning model for each classification result by the ADC processing unit 1202. The height calculation unit 205 reads out the model corresponding to the classification result by the ADC processing unit 1202 and outputs the height information of the foreign matter and the like included in the SEM image 200 by using the model (identifier). According to the configuration of FIG. 12, the foreign matters can be classified based on the feature that can be determined by using the two-dimensional image (feature having a two-dimensional shape of the foreign matter), and the height can be estimated by using the learning model appropriate for the classified foreign matter is obtained, so that the height can be estimated with high accuracy.

In the third embodiment, an example of switching the model according to the design data (layout) or the density of the circuit (the number of patterns or edges per unit area, or the like) is mainly described, but the present invention is not limited thereto, and the model may be switched to other model according to the parameter. For example, the learning is performed by using the teacher data in which the outputs of the plurality of shadow image detectors and the layout data (design data) are set as an input and the height information of the foreign matter obtained by the AFM or the like is set as an output. The output of the plurality of shadow image detectors and the layout data corresponding to the coordinates read out from the design data 1004 by referring to the coordinate information output by the higher level foreign matter inspection device 1002 are input to the identifier 201. Therefore, it is possible to estimate the height information. In such a learning model, since the structure for the height estimation changes based on the shape and the density of the layout, high accurate height estimation can be performed.

As a deep neural network method of generating height map data by the AFM from the image data, a semantic segmentating method of converting data in pixel units with a multi-step encoder/decoder using a pooling layer and an image generating method of generating data in pixel unit using hostile generation learning can be applied.

Fourth Embodiment

FIG. 13 is a diagram illustrating an example of a display screen that displays both the estimation result of the height using the learning model and the estimated accuracy output from the learning model. This display screen is displayed, for example, on the display device of the input/output device 206 illustrated in FIG. 10. The processing unit 1005 reads out necessary information from the computer-readable medium 1006 and displays a screen as illustrated in FIG. 13. By referring to this screen, the user determines whether or not to generate further the teacher data.

In FIG. 13, height information (height) 1303 estimated by using the learning model and an estimated accuracy 1304 (accuracy) are displayed for each foreign matter to which the identification information (ID) 1301 is designated. Coordinate information (coordinate) 1305 is the coordinate of the foreign matter. The estimated accuracy together with the height information is output from the learning model by the identifier module 1010. A SEM image field 1302 is provided with a link for reading out the SEM image and by selecting the link, it is displayed on the display device that the SEM image is read out from the storage medium. The estimated accuracy can be calculated, for example, by using an evaluation value relative to other estimation result candidates when the identifier 201 outputs the estimation result. The accuracy may be obtained by using another appropriate method. The same applies to the following embodiments.

It can be grasped from the screen as illustrated in FIG. 13 that it is necessary to update the teacher data by using the high accurate height measurement device such as the AFM for the foreign matter having low estimated accuracy, and thus, update determination of the learning model can be efficiently performed. In addition, the screen of FIG. 13 is provided with a field of the AFM (measurement) 1306, and by selecting the field, it is configured so that the coordinate information 1305 of the selected the foreign matter and the information of the SEM image field 1302 can be transmitted to the control device of the AFM. According to such a configuration, it is possible to easily set the conditions of the height measurement device for obtaining the information required for updating the teacher data. In addition, by allowing a predetermined threshold value to be set to the estimated accuracy and displaying the foreign matter below the threshold value separately from other foreign matters, it is possible to easily visually recognize the foreign matter that needs to be updated in the teacher data.

Fifth Embodiment

In recent years, the semiconductor devices have become more multi-layered with miniaturization (scaling), and thus, the number of layers also increases. In addition, as the scaling proceeds, the size of the foreign matter adhering to the semiconductor wafer becomes large relative to the pattern formed on the semiconductor wafer, and thus, it is expected that the need for evaluation the correlation between the foreign matter adhering more than ever and the performance of the device increases. In addition, it can be considered that there is a possibility that the foreign matter adhering after a certain manufacturing process may influence the performance of the pattern formed in the subsequent manufacturing process. In the fifth embodiment of the present disclosure, a system that evaluates the influence of the foreign matter adhering to a certain layer on another layer generated in the subsequent manufacturing process will be described.

The system according to the fifth embodiment performs the learning by using the teacher data in which the data obtained based on the irradiation of the first layer with the charged particle beam or the feature extracted from the data is set as an input and the pattern images and the feature at a position corresponding to the first position of the second layer manufactured in the process later than the manufacturing process of manufacturing the first layer are set as an output. By inputting the image data at the first position or the feature extracted from the data to the learning model, the image or the feature at the position corresponding to the first position of the second layer is output.

FIG. 14 is a flowchart illustrating a process of generating the learning model of the identifier 201 in the fifth embodiment. As the system configuration, the system configuration illustrated in FIG. 10 can be used. The coordinates (first position) of the foreign matter adhering to the semiconductor wafer generated in the manufacturing process of the first layer are specified by using the higher level foreign matter inspection device 1002 illustrated in FIG. 10 (S1401). Next, the semiconductor wafer is introduced to the imaging unit 301, and the foreign matter adhering to the first position is measured or inspected by using the imaging unit 301 (S1402). At this time, the AFM may be used as a measurement tool. The imaging unit 301 controls at least one of the sample stage 313 (refer to FIG. 3) and the deflector for moving the field of view so as to irradiate the coordinate position with the electron beam based on the coordinate information specified by the higher level foreign matter inspection device 1002. The image data obtained by the inspection measurement and the feature amount extracted from the image data are acquired (S1403). The data and the feature become the input data of the learning model described later.

As the image data used in FIG. 14, an image generated based on the output of the shadow image detectors arranged in the multiple directions described in the second embodiment can be preferably used, but the present invention is not limited thereto, a general secondary electron image and an image or a continuous image (moving image) obtained by scanning with a tilt beam may be used. As the feature, there are the size and dimensions of the foreign matter, the size and aspect ratio of the brightness region indicating the edge portion of the foreign matter, the type of the foreign matter shape, the material (specified by using an EDX detector or the like), and the like.

Next, after the manufacturing process for the second layer formed on the first layer, the measurement or inspection for the first position of the second layer is performed by scanning the first position of the second layer with the electron beam or scanning with the probe of the AFM (S1404). The imaging unit 301 and the AFM can move the field of view by using the coordinate information of the first position acquired by the higher level foreign matter inspection device 1002.

The computer system 202 acquires the feature such as the image data and the patterns extracted from the image based on the signal acquired by the imaging unit 301 or the like (S1405). The feature acquired in S1404 may be one or more the parameters for evaluating the performance of the pattern, such as the dimension value (CD value) of the pattern formed on the second layer of the semiconductor wafer, the shape, the amount of deformation of the shape, the degree of deviation of the edge position from the design data, and the size of the region indicating abnormalities of these features (for example, deformation and the like equal to or larger than the predetermined threshold is accepted), and the feature may be sample surface information such as the height information obtained by the AFM.

FIG. 15 is a diagram illustrating a state in which the foreign matter placed on the first layer pushes up the second layer. In this manner, since it is considered that the region directly above and around the foreign matter is pushed up the foreign matter, in order to appropriately evaluate the influence of the foreign matter, it is preferable to set the data including the feature and images of the peripheral region as the output data of the neural network. Therefore, with respect to the image data and a feature acquired on the second layer, it is preferable to extract the feature of a region having a size wider than the foreign matter size so that an index value of the influence of the foreign matter placed on the first layer on the second layer becomes the output of the neural network.

By generating the learning model based on the input data and the output data (S1406) as described above, it is possible to construct the learning model capable of estimating the data indicating how the foreign matter placed on the first layer influences the second layer provided on the upper layer of the first layer. In addition, since it is considered that the influence of the foreign matter may change according to the layout of the pattern formed on the second layer and the pattern density, it is preferable to prepare the plurality of models according to the type and density of the pattern layout.

As a deep neural network method of generating the data of the second layer from the image data of the first layer, a semantic segmentating method of converting data in pixel units with a multi-step encoder/decoder using a pooling layer and an image generating method of generating data in pixel unit using hostile generation learning can be applied.

FIG. 16 is a flowchart illustrating a process of estimating the sample information by using the learning model generated as described above. First, the semiconductor wafer on which the first layer is formed is introduced to the higher level foreign matter inspection device 1002, and the coordinate information of the foreign matter is acquired (S1601). Next, the sample stage or the like in the imaging unit 301 is driven so that the coordinates are irradiated with the electron beam based on the acquired coordinate information of the foreign matter, and the measurement or the inspection of the foreign matter is performed (S1602).

On the other hand, by referring to the design data 1004 based on the acquired coordinate information, the computer system 202 acquires layout information of the second layer corresponding to the coordinate information and selects the model stored according to the type of the layout (S1603). As described above, since the influence of the foreign matter on other layers is changed according to the density of the patterns and the type of the layout, a plurality of the models are prepared in advance according to the layout, pattern density, or the like, and an appropriate model is selected according to the foreign matter coordinates.

The computer system 202 outputs the estimation information of the second layer corresponding to the coordinate information by inputting at least one of the image data and the feature to the selected model (S1604 and S1605).

FIG. 17 is a diagram illustrating a display example of the output data (estimation information). For example, the input/output device 206 can display the screen. Herein, an example is illustrated in which the electron microscope image of the foreign matter on the first layer obtained by the imaging unit 301 and the estimation result of the influence of the foreign matter on the second layer are superimposed. More specifically, FIG. 17 illustrates an example in which a deformation rate and an estimated accuracy of an actual pattern with respect to a reference pattern are displayed with the foreign matter images superimposed. For example, the deformation rate can be obtained from a difference between a pattern edge included in the electron microscope image of the pattern formed on the foreign matter after the second layer is formed and an edge of the design data. The learning model is learned in advance by using the teacher data in which this value is set as an output.

FIG. 17 illustrates an example in which pattern information estimation using the learning model X is performed on the left half of the foreign matter, and pattern information estimation using the learning model Y is performed on the right half thereof. Since it is considered that, when the foreign matter adhering to the first layer is stretched over two pattern regions having different density regions of the second layer, the influence of the foreign matter on each pattern region is different, it is possible to appropriately evaluate the influence of the foreign matter on the second layer by performing the estimation using an appropriate model according to the region.

Figure 18:
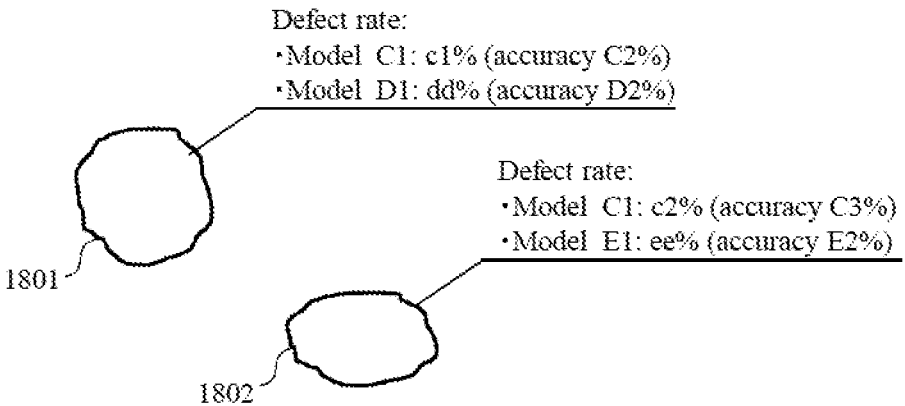
FIG. 18 is a diagram illustrating a display example when a defect rate is output from a learning model.

FIG. 18 is a diagram illustrating a display example when the defect rate is output from the learning model. According to the display example of FIG. 18, it is possible to grasp the degree to which the foreign matter adhering to the first layer causes the pattern defect of the second layer to occur. The defects are, for example, disconnections or short-circuits in wiring, and in the case of generating the learning model, the learning is performed by using the teacher data in which the inspection result of the defects on the second layer is set as an output. FIG. 18 illustrates an example in which the defect rate is estimated for one foreign matter by using the plurality of models, and the result is displayed. When a plurality of different layouts are superimposed on one foreign matter, due to such a display, it is possible to grasp the possibility that one foreign matter may cause the defects in other layers.

Sixth Embodiment

Figure 19:
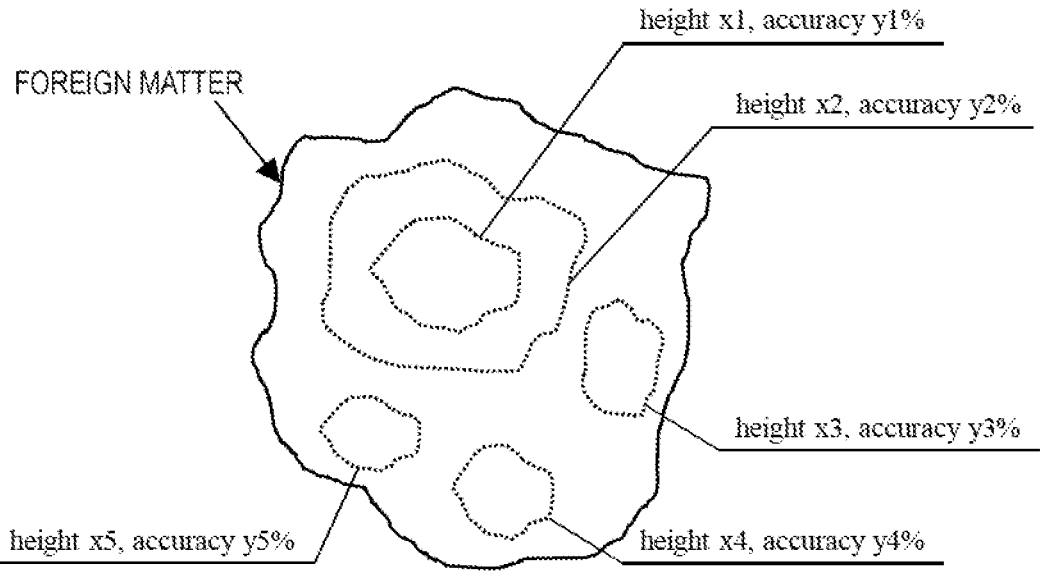
FIG. 19 is a diagram illustrating a display example of the foreign matter height estimation result.

FIG. 19 is a diagram illustrating a display example of a foreign matter height estimation result. In the example of FIG. 19, the height of each portion of the foreign matter and the accuracy thereof are output via the neural network. By displaying the height estimation result and the accuracy in units of a portion in this manner, for example, when the low accuracy region is surrounded by the high accuracy region, it can be estimated that the low accuracy region is equivalent to the high accuracy region in terms of height. The height of the foreign matter can be learned by the method described in the above-described embodiments.

Figure 20:
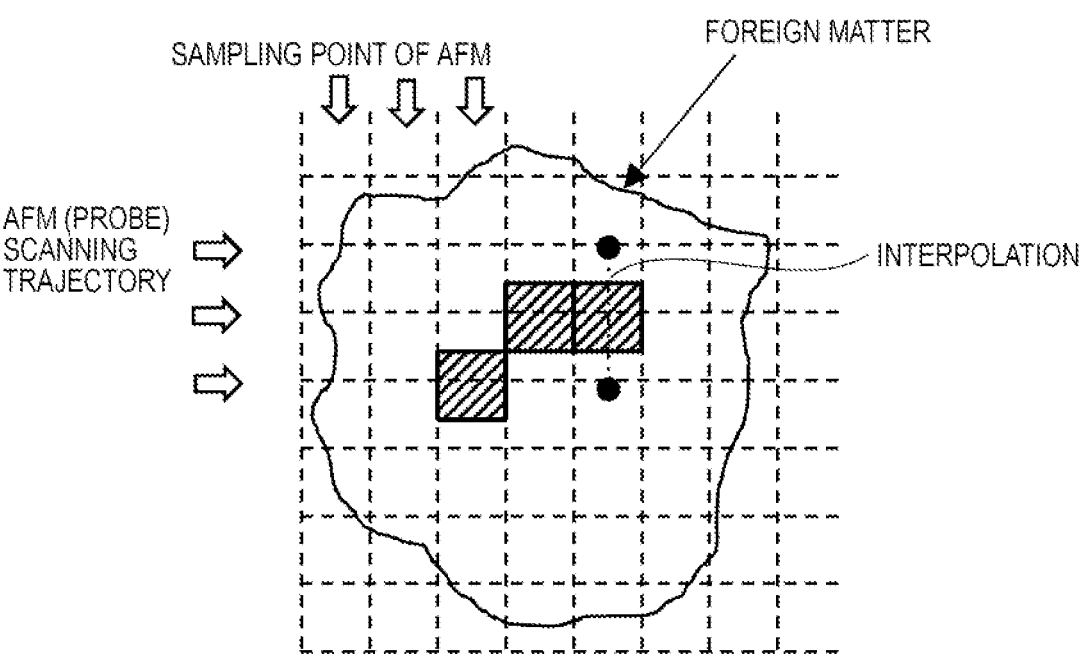
FIG. 20 is a diagram illustrating an example of a method of estimating a height of a region having low estimated accuracy based on height information of the region having a high estimated accuracy.

FIG. 20 is a diagram illustrating an example of a method of estimating the height of the region having a low estimated accuracy based on the height information of the region having a high estimated accuracy. A hatched portion indicates a region with low estimated accuracy, and the other regions indicate regions with relatively high estimated accuracy. As illustrated in the figure, it is possible to estimate the height of the region with low estimated accuracy by interpolating between the regions with high estimated accuracy so as to be stretched over the portion with low estimated accuracy. As a result estimated by interpolation or extrapolation, when the original estimation result and the result estimated by interpolation and the like are the same or equivalent (for example, at an error rate of n % or less), the learning is performed so that the estimated accuracy is increased, and when there is a deviation in the estimation result, the learning is performed so that the interpolation result is set as the estimation result. Therefore, it is possible to update the model so as to improve the estimated accuracy without actually performing re-measurement by using the AFM or the like.

Seventh Embodiment

In the seventh embodiment of the present disclosure, a method of updating the learning model for estimating the height from the output obtained by the charged particle beam device including the shadow image detectors as illustrated in FIG. 6 will be described. Specifically, a method of switching a model updating method according to the output of the shadow image detector will be described. As the system configuration, for example, the system configuration described in the second embodiment can be used.

Figure 21:
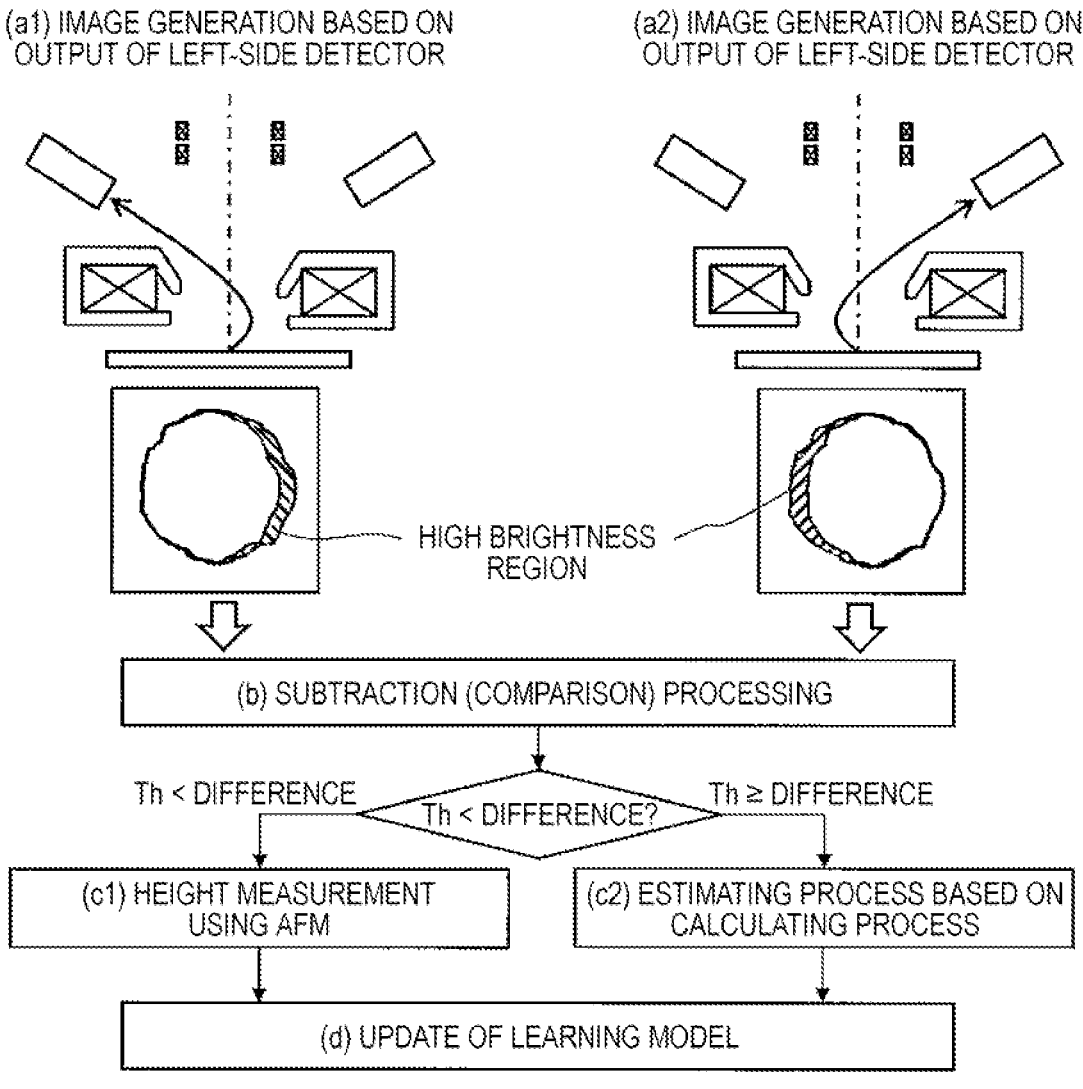
FIG. 21 is a diagram illustrating a procedure for updating a learning model of an identifier 201.

FIG. 21 is a diagram illustrating a procedure for updating the learning model of the identifier 201. In the seventh embodiment, as illustrated in FIG. 21, a scanning electron microscope including two detectors of a left-side detector and a right-side detector is described as an example, but the embodiment can be applied to a charged particle beam device including three or more detectors.

As illustrated in FIG. 21, the appearance of the image generated based on the output of the left-side detector and the appearance of the image generated based on the output of the right-side detector are different. For example, since the image generated based on the output of the left-side detector is emitted from the foreign matter to the right side of the paper and is generated based on the detection of the electrons deflected by the focusing operation of the objective lens, the image becomes an image having the right edge being emphasized (having high brightness) (a1). On the other hand, since the image generated based on the output of the right-side detector is opposite to that of the left-side detector, the image becomes an image having the left side edge being emphasized (a2). In addition, it is considered that the higher the height of the foreign matter, the larger the high brightness region. Furthermore, it is considered that, in the place where the output difference between the left and right side detectors is large, the shape of the foreign matter is complicated, and the estimation using the learning model cannot be appropriately performed. Therefore, in the seventh embodiment, the difference between the plurality of detectors is obtained (b), and when the difference exceeds a predetermined value, the coordinate information of the foreign matter is transmitted to the AFM, and the height is measured by the AFM (c1). When the difference is equal to or less than the predetermined value, the data of the portion having low estimated accuracy is updated based on the feature extraction of the estimation result without using the AFM such as the interpolation between the regions. Therefore, it is possible to efficiently update the learning model.

In FIG. 21, the model updating method for performing height measurement using the AFM when the difference between the outputs (or images) of the left and right detectors is large has been described, but it is considered that, when there is almost no output difference, the accuracy of the height estimation result based on the shadow image detector output is decreased. In order to perform highly accurate estimation on such a portion, the height measurement using the AFM may be performed, and the learning model may be learned by using the teacher data in which the result is set as an output.

Eighth Embodiment

Even when the image data and a feature obtained by the charged particle beam device and the measured values of the height are sufficiently learned, the amount of information between the two cases is significantly different, so that, in some cases, the accuracy of the height estimation may be decreased. By automatically determining such a case from the output data of the charged particle beam device, stable and high accurate measurement by combining the height estimation and the actual measurement becomes possible. Therefore, in an eighth embodiment of the present disclosure, described is a method of generating a learning model for determining whether or not the height can be estimated from the image data and a feature obtained by the charged particle beam device and measuring the height with stable accuracy by utilizing the learning model.

Figure 22:
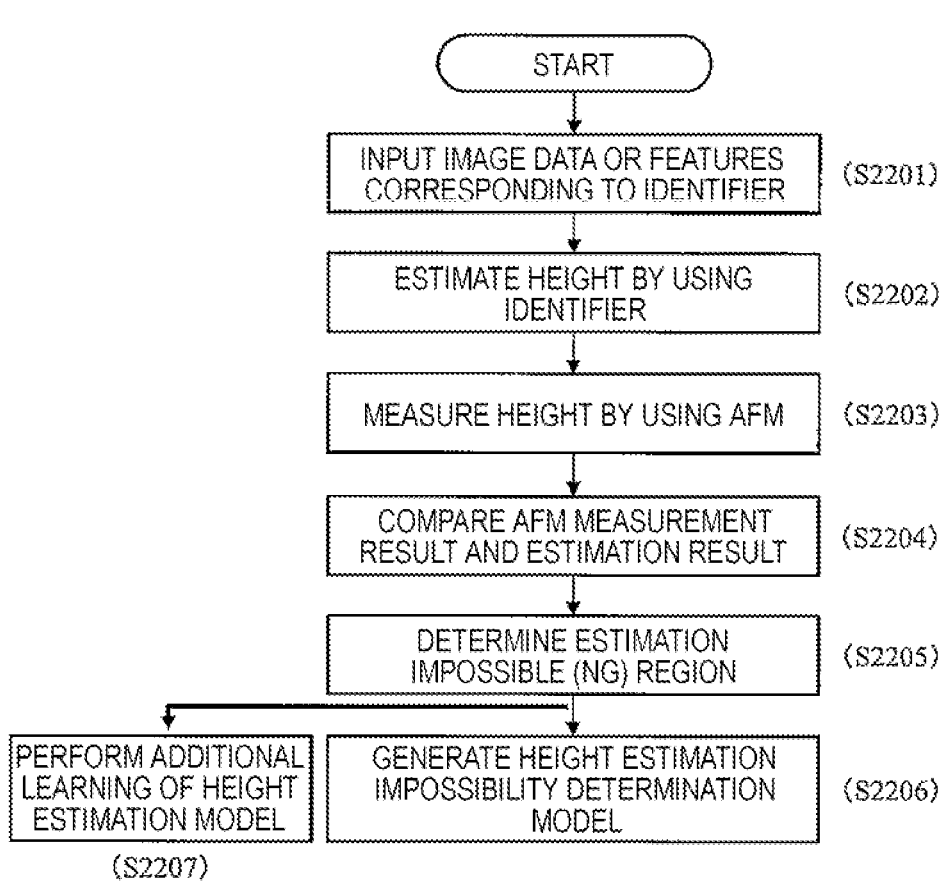
FIG. 22 is a flowchart illustrating a learning model generating process of determining whether or not height estimation is possible from image data and a feature obtained by a charged particle beam device.

FIG. 22 is a flowchart illustrating a process of generating the learning model for determining whether or not the height estimation is possible from image data and the feature obtained by the charged particle beam device. First, the image data and the feature obtained by the charged particle beam device are input (S2201). Next, the height estimation is performed by the identifier (S2202). Next, the height is measured by using the AFM (S2203). The estimated value and the measured height by the AFM are compared (S2204). When there is a sufficient deviation between the estimated value and the measured value, the portion is determined to be a portion of which height is difficult to estimate (S2205). Next, a height estimation impossibility determination model that outputs an estimation result indicating that the height is estimated is generated by machine learning by setting the image data or the feature information as an input. When the input is image data, the model extracts the regions where the height in the image is difficult to estimate and the regions where the height can be estimated, and when the input is the feature information, the model outputs whether or not the height can be estimated by using the feature. By utilizing the model, it is possible to determine whether the estimation can be performed or actual measurement needs to be performed by analyzing the input data. In addition, by performing additional learning of the height estimation by using the data of the portion of the height estimation NG, it is also possible to improve the accuracy of the height estimation.

Figure 23:
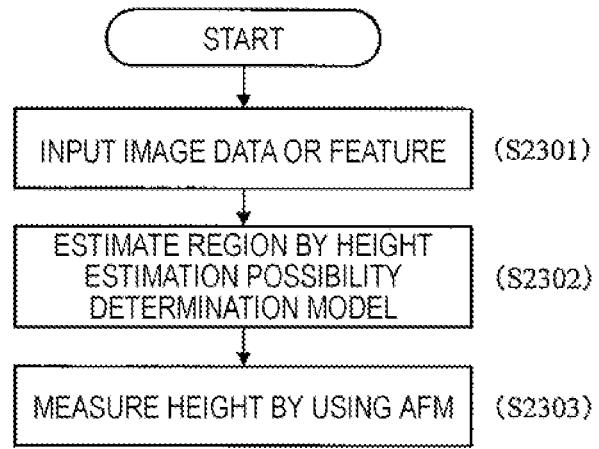
FIG. 23 is a flowchart illustrating a process of determining whether or not height estimation is possible from an output of a charged particle beam device by using a height estimation possibility determination model described with reference to FIG. 22 and actually measuring an NG portion with an AFM.

FIG. 23 is a flowchart illustrating a process of determining whether or not the height can be estimated from the output of the charged particle beam device by utilizing the height estimation possibility determination model described with reference to FIG. 22 and actually measuring the NG portion by the AFM. First, the image data and the feature information are input by the charged particle beam device (S2301). Next, the height estimation possibility is determined by using the height estimation possibility determination model (S2302). In the case where the height estimation is impossible, the height is measured by the AFM (S2303).

Ninth Embodiment

In the third embodiment, an example has been described in which the ADC is executed as a pre-treatment and the height of the foreign matter is estimated by using the learning model corresponding to the classification result. In the ninth embodiment of the present disclosure, an example is described in which the ADC process is performed by using the learning model.

Figure 24:
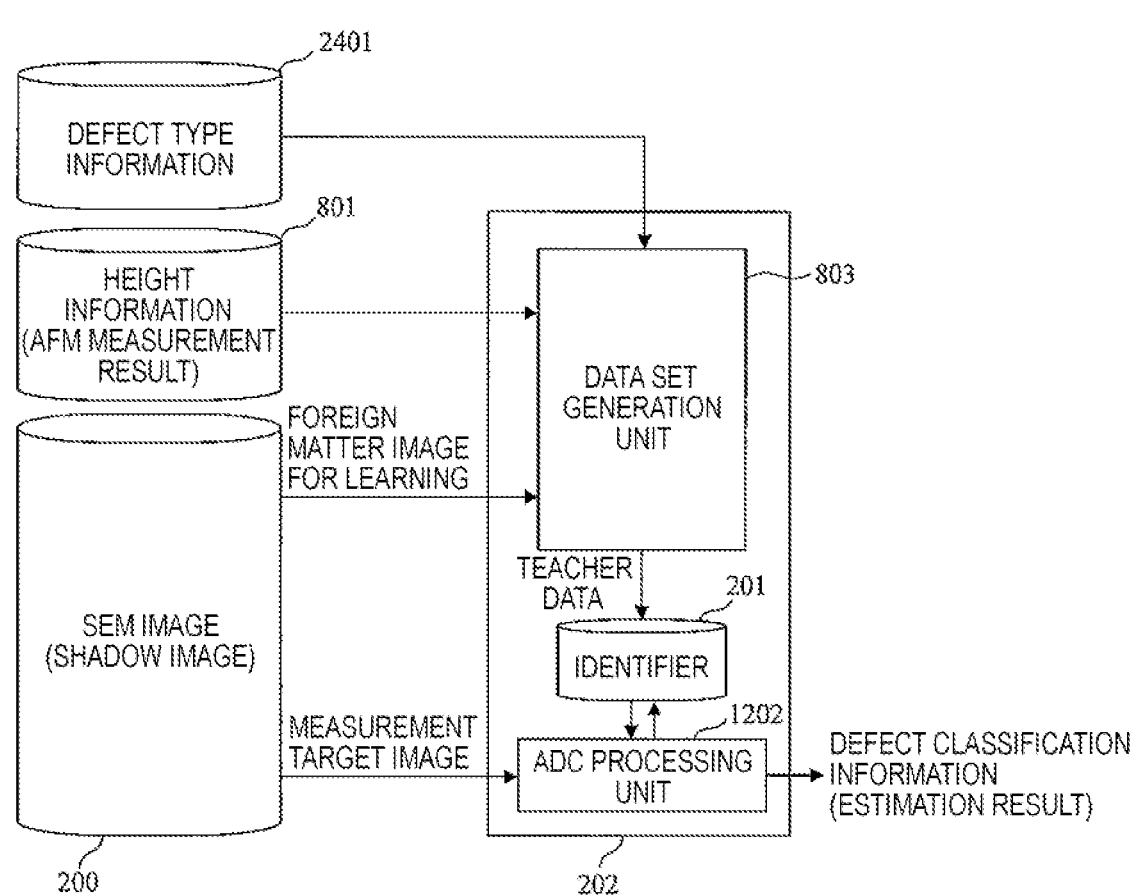
FIG. 24 is a diagram illustrating an example of a computer system that performs defect classification by using a shadow image as the input data.

FIG. 24 is a diagram illustrating an example of a computer system that performs defect classification by using a shadow image as the input data. In FIG. 24, the identifier 201 performs the learning in advance by using the teacher data in which the SEM image 200 (shadow image) is set as an input and the height information 801 (AFM measurement result) and the defect type information 2401 is set as an output. The identifier 201 is used to classify the defects or the foreign matter. As an estimation result, not only the type of defect (disconnection, short-circuit, foreign matter, shape of the foreign matter, or the like) but also the height information can be output, and thus, for example, the influence of the defect, or the like on the next process can also be estimated.

Figure 25:
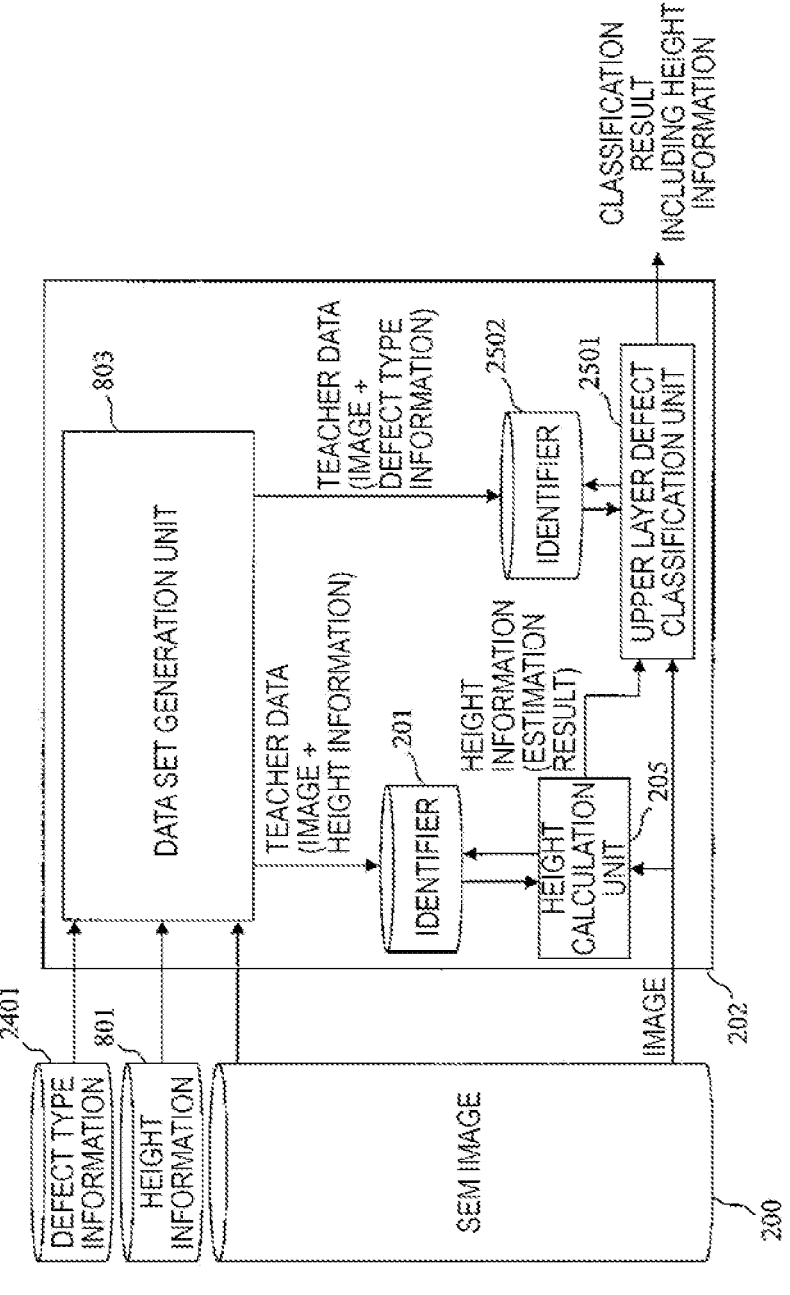
FIG. 25 is a configuration diagram of a computer system 202 in a ninth embodiment.

FIG. 25 is a configuration diagram of the computer system 202 according to the ninth embodiment. The system illustrated in FIG. 25 includes identifiers 201 and 2502. The identifier 201 performs learning by using the height information 801 of the foreign matter obtained by the AFM or the like and the data set of the SEM image 200 generated based on the output of the shadow image detectors as the teacher data. The identifier 2502 performs the learning by using the height information estimated by the height calculation unit 205, the image and the like generated based on the output of the shadow image detectors, and the data set of the defect type information 2401 as the teacher data. An upper layer defect classification unit 2501 executes defect classification by using the identifier 2502.

The upper layer defect classification unit 2501 estimates the type of defect of the pattern formed in the upper layer (second layer) by using the two-dimensional feature of the foreign matter included in the SEM image 200 of the lower layer (first layer) and the estimated height information (three-dimensional information) as an input. According to the system including the identifier 2502, it is possible to perform appropriate classification according to the feature of defects. In order to learn the identifier 2502, the SEM image such as the foreign matter image of the lower layer and the SEM image at the position of the upper layer corresponding to the foreign matter coordinates of the lower layer are acquired, and the identifier 2502 is learned by using the SEM image or the feature (type of defect) extracted from the image as a data set.

Figure 26:
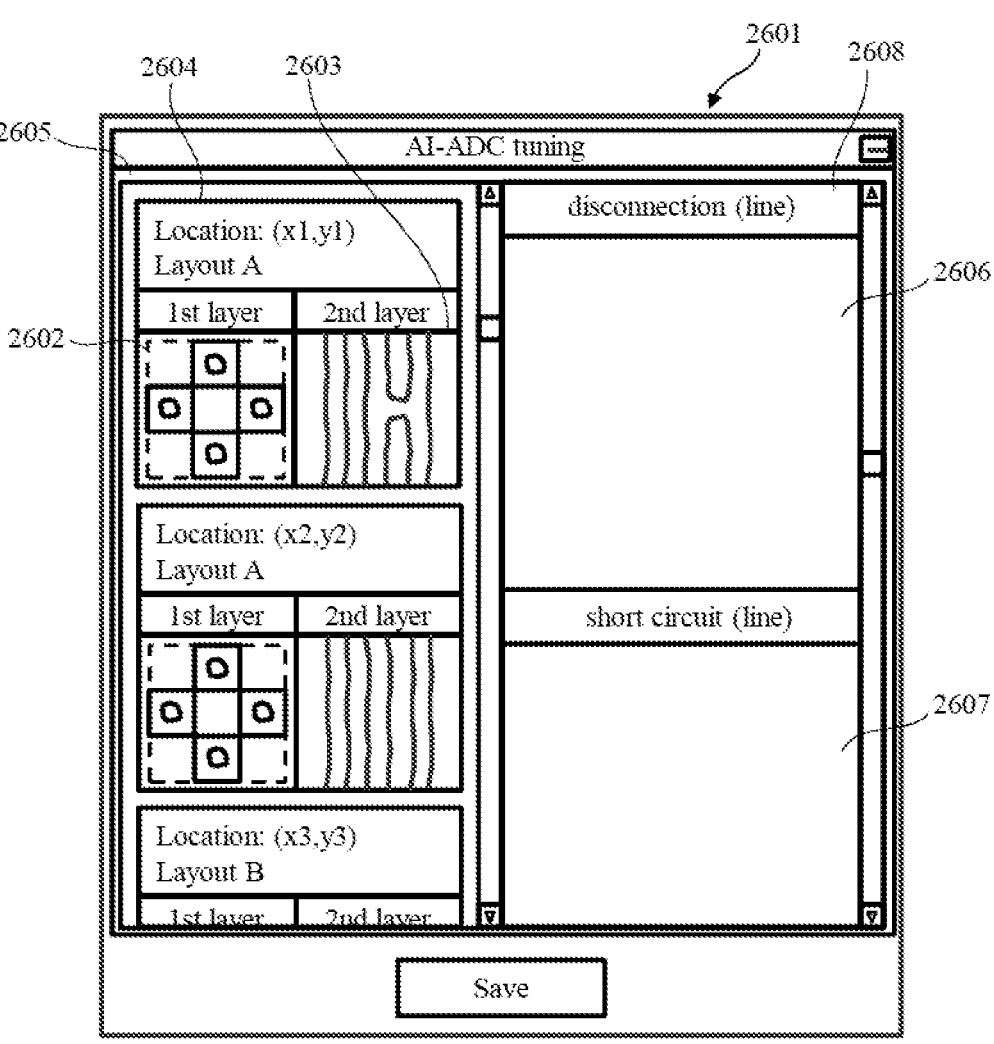
FIG. 26 is a diagram illustrating an example of a GUI screen for optimizing a learning model according to the ninth embodiment.

FIG. 26 is a diagram illustrating an example of a GUI screen for optimizing the learning model in the ninth embodiment. A GUI screen 2601 has a left field 2605 and a right field 2608. In the left field 2605, a plurality of thumbnails 2604 are displayed in which an SEM image 2602 of the lower layer that is the input of the data set and an SEM image 2603 of the upper layer at the same position as the foreign matter coordinates are displayed as one set. The right field 2608 is provided with input fields 2606 and 2607 for each type of defect.

The operator can update the learning data by looking at the SEM image 2603 of the upper layer, determining the type of defect (the SEM image 2603 is a state in which the line patterns are short-circuited), and moving the thumbnail 2604 to the input field of the corresponding type of defect in the right field 2608 by using a pointing device or the like. The data set generation unit 803 generates a data set in which the SEM image 2602 of the lower layer included in the thumbnail 2604 or the feature extracted from the SEM image is set as am input and the type of defect in the input field in which the thumbnail 2604 is input is set as an output. This data set is set as the teacher data of the identifier 2502. According to such a configuration, it is possible to specify the type of defect of the upper layer from the foreign matter image of the lower layer.

Tenth Embodiment

In a tenth embodiment of the present disclosure, an example will be described in which an estimation model for estimating what happens in the upper layer when the foreign matter exists in the lower layer is generated, and the situation of the upper layer is estimated by using the estimation model. The input layer in the neural network used in the tenth embodiment is input with (a) first data including at least one of design data (design information) of the upper layer (second layer) and a feature (for example, a line width of a pattern, an area of a pattern, distance between patterns, or the like) extracted from the design data and (b) second data including at least one of an image of the lower layer (first layer) obtained by an imaging system such as a scanning electron microscope illustrated in FIGS. 3 and 6 and a feature extracted from the second image. It is preferable that a lower layer image is generated based on the output of the plurality of shadow image detectors capable of grasping the foreign matter and the like three-dimensionally. As the feature extracted from the second image, for example, the shape and size of the foreign matter, the brightness information, the difference data between shadow image detectors, and the like can be considered.

The intermediate layer of the neural network used in the tenth embodiment performs the learning by using the teacher data in which the first data and the second data are set as an input and the third data including at least one of the image of the upper layer and the feature of the upper layer is set as an output. The output layer generates the output data based on the output of the intermediate layer.

Figure 27:
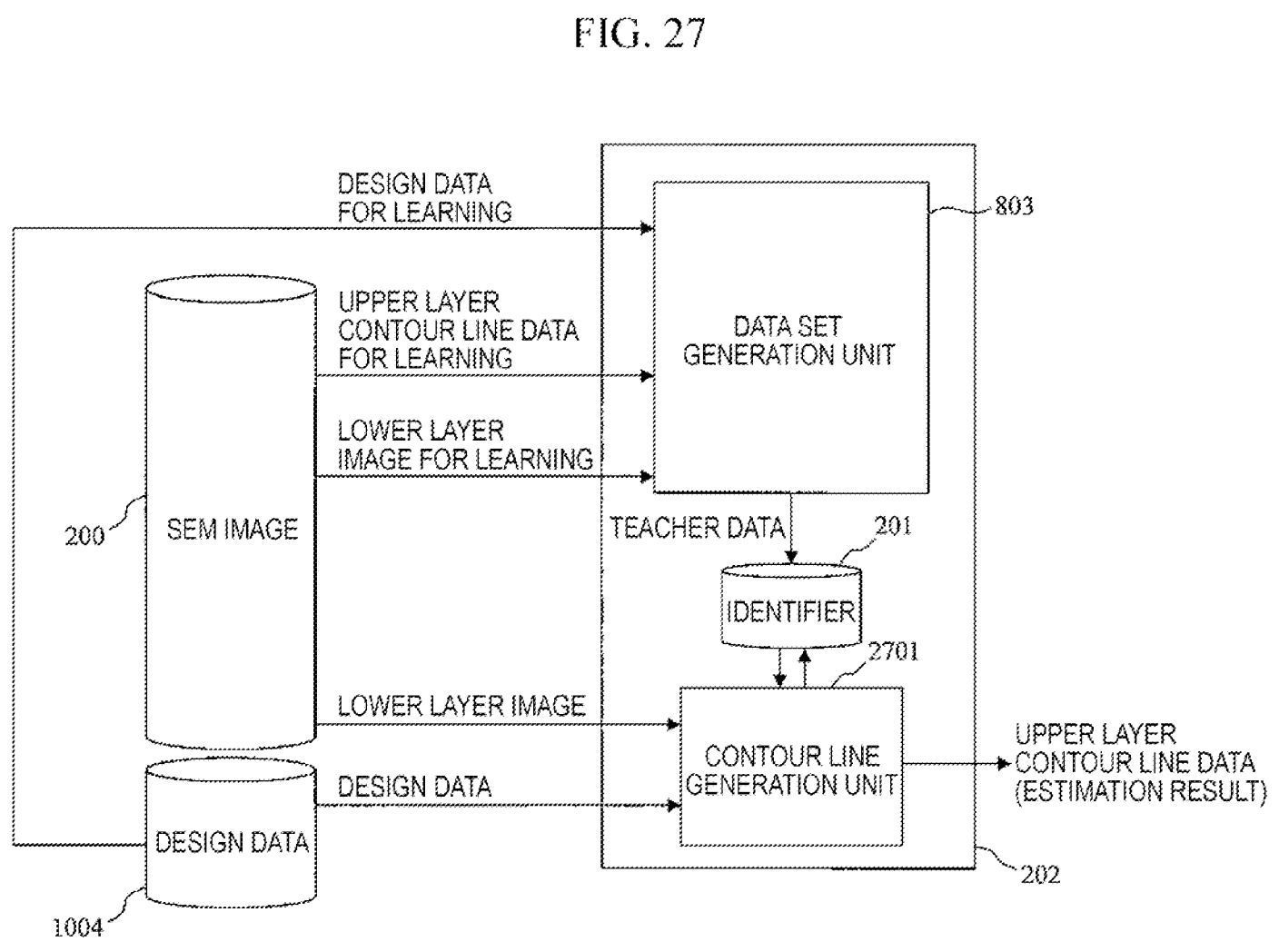

FIG. 27 is a diagram illustrating an example of a computer system 202 including a module (identifier 201) including the estimation model as described above. The data set generation unit 803 receives the design data 1004 as learning data. The data set generation unit 803 further receives an upper layer contour line image and the lower layer image as the learning data from the SEM image 200. The data set generation unit 803 uses this data to generate the teacher data and allows the identifier 201 to be learned. The contour line generation unit 2701 receives the lower layer image and the design data 1004 as an input and estimates the contour line of the upper layer by inputting the lower layer image and the design data 1004 to the identifier 201.

Figure 28:
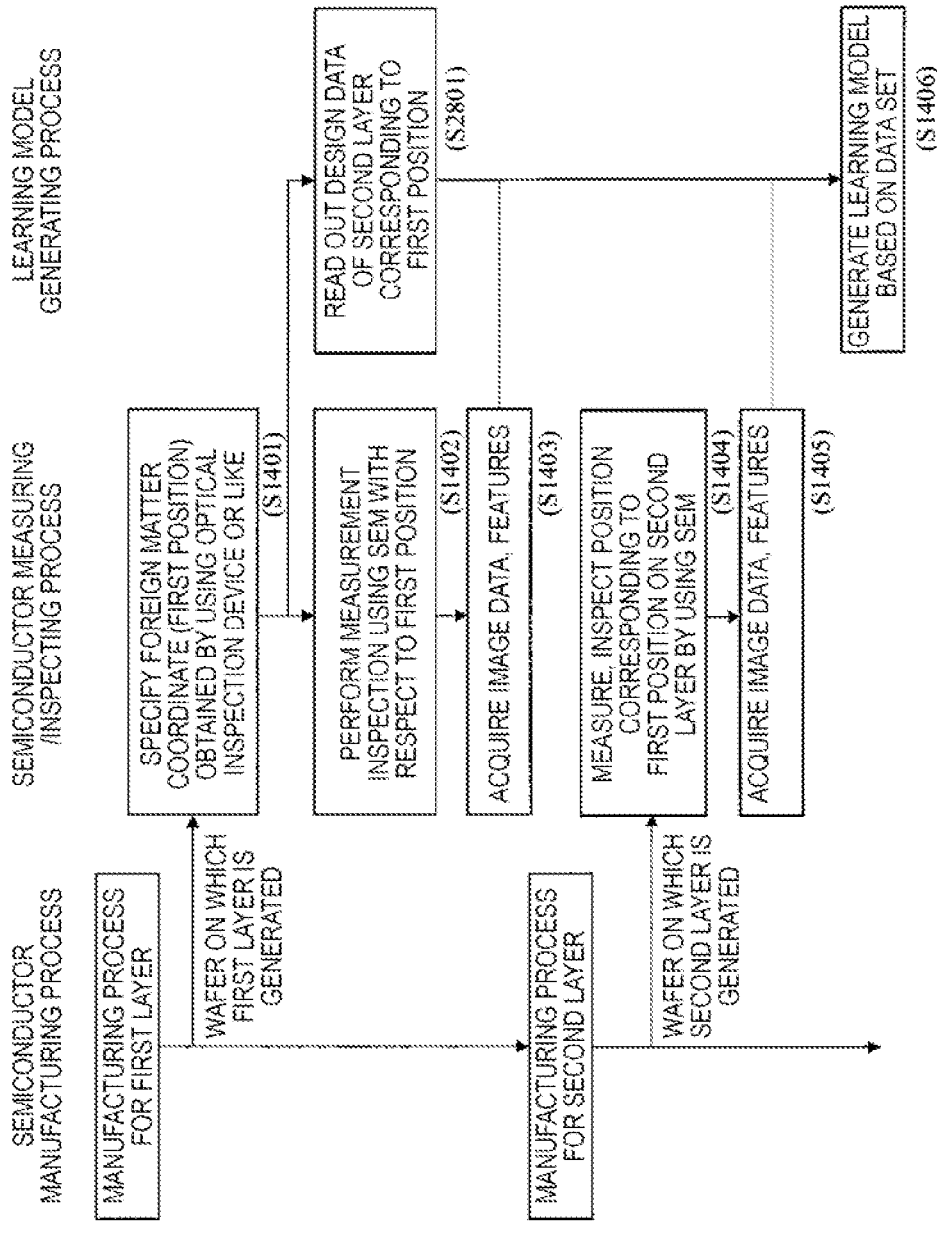
FIG. 28 is a flowchart illustrating a learning process according to a tenth embodiment.

FIG. 28 is a flowchart illustrating the learning process according to the tenth embodiment. First, the coordinates (first position) of the foreign matter adhering to the semiconductor wafer generated in the manufacturing process for the first layer are specified by using the higher level foreign matter inspection device 1002 as illustrated in FIG. 10 (S1401). Next, the semiconductor wafer is introduced to the imaging unit 301, and the measurement or the inspection using the imaging unit 301 is executed for the foreign matter adhering to the first position (S1402). Herein, for example, the foreign matter image is generated from the outputs of the plurality of shadow image detectors. As will be described later, the foreign matter image is used to generate the teacher data as the data set, but the feature extracted from the image other than the image may be used to generate the data set. Furthermore, the computer system 202 reads out the design data (layout data) of the pattern corresponding to the first position from the design data 1004 (S2801).

Next, the computer system 202 acquires the image of the first position of the second layer after the second layer is stacked on the first layer (S1404, S1405).

The identifier 201 is learned by using a data set of the foreign matter image data of the lower layer, the design data of the upper layer, and the image data of the upper layer (or contour line data of the pattern extracted from the image data) obtained through the above-described processes as the teacher data (S1406). The data set that becomes the teacher data includes the foreign matter image located in the lower layer, the design data (layout data) illustrating the ideal shape of the pattern, and the image data of the same pattern as the design data of the pattern of the upper layer influenced by the foreign matter (or the contour line data extracted by thinning the edges included in the image). That is, the data set includes a pattern image (layout data of the upper layer) that is not influenced by the foreign matter, a pattern image (the real image or the contour line data of a pattern of the upper layer) that is influenced by the foreign matter, and factors that deform the pattern, and an image of the foreign matter that becomes a cause of deforming the pattern or the like, and thus, the data set becomes the teacher data that includes the shape before deformation, the cause of deformation, and the shape after deformation. Therefore, it is possible to construct the learning model for estimating the influence of the foreign matter of the lower layer on the upper layer.

In the above-described embodiments, an example has been described in which the learning model is learned by using the teacher data in which the SEM image of the foreign matter of the lower layer and the design data of the upper layer is set as an input and the SEM image of the upper layer (or the contour line data extracted from the SEM image) is set as an output, the learning model may be learned by adding the information about the manufacturing process and the imaging conditions of the SEM as an input and adding the fatality or the like of the pattern of the upper layer as an output.

By preparing the wafer which a relatively large amount of the foreign matter adheres to and acquires the image of the foreign matter of the lower layer, the SEM image of the pattern of the upper layer corresponding to the position where the foreign matter adheres, or the like, a larger data set that becomes the teacher data can be prepared.

Modified Example of Present Disclosure

The present disclosure is not limited to the above-described embodiments and includes various modified examples. For example, the above embodiments have been described in detail in order to explain the present invention for the easy understanding, and the embodiments are not necessarily limited to those having all the described configurations. In addition, a portion of the configuration of one embodiment can be replaced with a configuration of another embodiment, and a configuration of another embodiment can be added to a configuration of one embodiment. In addition, with respect to a portion of the configuration of each embodiment, addition, deletion, and replacement with another configuration are available.

In the above-described embodiments, the identifier 201 included in the computer system 202 is configured by a function of outputting values according to the learning result when the values are input to the storage unit 305 that stores the learning result and each unit. This function of the identifier 201 and other functional units included in the computer system 202 may be configured by using hardware such as a circuit device that implements such a function or may be configured by allowing a calculation device to execute software that implements such a function.

REFERENCE SIGNS LIST

201: identifier
202: computer system
203: length measurement value/area value calculation unit
204: brightness evaluation unit
205: height calculation unit
206: input/output device
301: imaging unit
302: overall control unit
303: signal processing unit
304: input/output unit
305: storage unit
306: electron gun
307: electron beam
308: focusing lens
309: focusing lens

22

310: deflector
311: objective lens
312: sample
313: sample stage
314: emitted electrons
315: lower detector
316: upper detector
317: energy filter
318: blanking deflector
319: blanking electrode

The invention claimed is:

1. A structure estimation system that estimates, from an observation image of a sample acquired by a charged particle beam apparatus, information about a depth or a height corresponding to the observation image on the sample or to a feature amount extracted from the observation image by one or more computer systems,
    wherein the structure estimation system includes the one or more computer systems and the charged particle beam apparatus configured to irradiate the sample with a charged particle beam, the charged particle beam apparatus including a plurality of shadow image detectors arranged in a direction tilted and axis-symmetrically with respect to a beam optical axis of the charged particle beam to obtain structure data about the structure of the sample,
    wherein the one or more computer systems include a non-transitory computer-readable medium storing a plurality of modules for implementing one or more functions implemented including at least a calculation module,
    wherein the one or more computer systems include an identifier that outputs information about the depth or the height corresponding to the observation image or to the feature amount extracted from the observation image,
    wherein the identifier is configured to receive as an input a plurality of types of background images in which an image is acquired for each of a plurality of different layouts and also to receive as an input a plurality of types of foreign object images acquired for each of a plurality of different signal processing conditions, and is configured to output information about the depth or the height corresponding to the observation image or to the feature amount extracted from the observation image, and
    wherein the calculation module acquires, from the identifier, information about the depth or the height corresponding to the observation image or to the feature amount extracted from the observation image by inputting the background images and the foreign object images to the identifier.

2. The structure estimation system according to claim 1, wherein the feature amount includes information about brightness of the observation image of the structure of the sample, and
    wherein the feature amount includes information about a size or an area of the structure of the sample.

3. The structure estimation system according to claim 1, wherein the information on the depth is information on whether the depth is deeper or shallower than a predetermined reference value, and
    wherein the calculation module outputs an estimation result of whether the depth is deeper or shallower than the predetermined reference value.

4. The structure estimation system according to claim 1, wherein the computer system acquires the plurality of types of foreign object images under different signal processing conditions with respect to one foreign object placed on the sample.

5. The structure estimation system according to claim 1, wherein the background image is an image of the sample on which a pattern is formed through a predetermined manufacturing process.

6. The structure estimation system according to claim 4, wherein the plurality of types of background images is acquired under the different signal processing conditions, under which the plurality of types of foreign object images is acquired.

7. The structure estimation system according to claim 1, wherein the identifier is a learner of any one of a neural network, a regression tree, and a Bayesian identifier.

8. The structure estimation system according to claim 7, wherein the learner performs a learning process using training data in advance, the training data being configured such that the learner is configured to receive as an input the plurality of types of background images in which an image is acquired for each of different layouts and also to receive as an input the plurality of types of foreign object images acquired for each of different signal processing conditions, and is configured to output information about the depth or the height corresponding to the observation image or to the feature amount extracted from the observation image.

9. A structure estimation system that estimates, from an observation image of a sample acquired by a charged particle beam apparatus, information about a depth or a height corresponding to the observation image on the sample or to a feature amount extracted from the observation image by one or more computer systems, wherein the structure estimation system includes the one or more computer systems and the charged particle beam apparatus configured to irradiate the sample with a charged particle beam, the charged particle beam apparatus including a plurality of shadow image detectors arranged in a direction tilted and axis-symmetrically with respect to a beam optical axis of the charged particle beam to obtain structure data about the structure of the sample, wherein the one or more computer systems include a non-transitory computer-readable medium storing a plurality of modules for implementing one or more functions implemented including at least a calculation module, wherein the one or more computer systems include an identifier that outputs information about the depth or the height corresponding to the observation image or to the feature amount extracted from the observation image, wherein the identifier is configured to receive as an input a composite image obtained by using a plurality of types of background images in which an image is acquired for each of a plurality of different layouts and also by using a plurality of types of foreign object images acquired for each of a plurality of different signal processing conditions, and is configured to output information about the depth or the height corresponding to the observation image or to the feature amount extracted from the observation image, and wherein the calculation module acquires, from the identifier, information about the depth or the height corresponding to the observation image or to the feature amount extracted from the observation image by inputting the composite image to the identifier.

10. A structure estimation system for estimating, from data obtained by a charged particle beam apparatus, information about a depth or a height of a pattern formed on a structure of a sample, wherein the structure estimation system includes one or more computer systems and the charged particle beam apparatus configured to irradiate the sample with a charged particle beam, the charged particle beam apparatus including a plurality of shadow image detectors arranged in a direction tilted and axis-symmetrically with respect to a beam optical axis of the charged particle beam to obtain structure data about the structure of the sample, wherein the one or more computer systems include a non-transitory computer-readable medium storing a plurality of modules for implementing one or more functions implemented including at least a calculation module, wherein the one or more computer systems include an identifier that outputs information about the depth or the height of the pattern formed on the structure of the sample, wherein the identifier is configured to receive as an input at least one of: an output of the multiple direction detector, which is data obtained by the charged particle beam apparatus, an image formed based on the output, or a feature of the pattern extracted from the image, and is configured to output information about the depth or the height of the pattern formed on the structure of the sample, and wherein the calculation module acquires, from the identifier, information about the depth or the height of the pattern formed on the structure of the sample by inputting to the identifier at least one of: the output of the multiple direction detector, the image formed based on the output, or the feature of the pattern extracted from the image.

11. The structure estimation system according to claim 10, wherein the feature of the pattern extracted from the image is a parameter indicating at least one of:

a brightness value of the pattern;

a size value of the pattern;

an evaluation value of a shape of the pattern, and a deformation amount of the shape of the pattern; and an evaluation value of quality of the pattern.

* * * * *